US010662435B2

(12) United States Patent
Lu et al.

(10) Patent No.: US 10,662,435 B2
(45) Date of Patent: May 26, 2020

(54) PLANTS HAVING ALTERED AGRONOMIC CHARACTERISTICS UNDER ABIOTIC STRESS CONDITIONS AND RELATED CONSTRUCTS AND METHODS INVOLVING GENES ENCODING NAC3/ONAC067 POLYPEPTIDES

(71) Applicant: PIONEER OVERSEAS CORPORATION, Johnston, IA (US)

(72) Inventors: Guihua Lu, Beijing (CN); Yang Gao, Beijing (CN); Cong Li, Beijing (CN); Guanfan Mao, Beijing (CN); Wei Wang, Beijing (CN); Xiping Wang, Beijing (CN); Changgui Wang, Beijing (CN)

(73) Assignee: PIONEER OVERSEAS CORPORATION, Johnston, IA (US)

( * ) Notice: Subject to any disclaimer, the term of this patent is extended or adjusted under 35 U.S.C. 154(b) by 0 days.

(21) Appl. No.: 15/316,602

(22) PCT Filed: Jul. 2, 2015

(86) PCT No.: PCT/CN2015/083231
§ 371 (c)(1),
(2) Date: Dec. 6, 2016

(87) PCT Pub. No.: WO2016/000643
PCT Pub. Date: Jan. 7, 2016

(65) Prior Publication Data
US 2017/0198300 A1    Jul. 13, 2017

(30) Foreign Application Priority Data
Jul. 3, 2014 (WO) ................ PCT/CN2014/081596

(51) Int. Cl.
*C12N 15/82* (2006.01)
*C07K 14/415* (2006.01)
(52) U.S. Cl.
CPC ........ *C12N 15/8271* (2013.01); *C07K 14/415* (2013.01); *C12N 15/8227* (2013.01); *C12N 15/8261* (2013.01); *C12N 15/8273* (2013.01)
(58) Field of Classification Search
None
See application file for complete search history.

(56) References Cited

U.S. PATENT DOCUMENTS

2004/0123343 A1   6/2004 La Rosa et al.
2009/0276918 A1*  11/2009 Choi .................. C12N 15/8261
                                                      800/278

FOREIGN PATENT DOCUMENTS

CN        102465114        5/2012
WO        2007144190 A2   12/2007
WO    WO 2012065528 A1 *  5/2012    ......... C12N 15/8227

OTHER PUBLICATIONS

UniProt Accession Q7EZT1, integrated on Dec. 20, 2005. (Year: 2005).*
Olsen et al. Trends in plant science 10.2 (2005): 79-87. (Year: 2005).*
Distelfeld et al. Plant Mol Biol (2012) 78:515-524. (Year: 2012).*
Nakashima et al. Biochimica et Biophysica Acta 1819 (2012) 97-103. (Year: 2012).*
GenBank Accession AP004572 entered Dec. 19, 2001. (Year: 2001).*
Guo et al. (2004, Proc. Natl. Acad. Sci. USA 101: 9205-9210). (Year: 2004).*
International Search report PCT/CN2015/0833231 dated Sep. 30, 2015.
OsNAC3 protein GenBank database accession No. BAA89797.1, Jan. 22, 2000.
OsNAC3 protein GenBank database accession No. BAC10231.1, Feb. 16, 2008.
Ooka, H. et al, "Comprehensive Analysis of NAC Family Genes in Oryza sativa and Arabidopsis thaliana" DNA Research vol. 10, Dec. 31, 2003, 239-247.
Takasaki, H. et al. "The abiotic stress-responsive NAC-type transctiption factor OsNAC5 regulates stress-inducible genes and stress tolerance in rice" Mol Genet Genomics, vol. 284, Jul. 15, 2010, 173-183.
Nakashima, K. et al. "NAC transcription factors in plant abiotic stress responses" Biochimica et Biophysica Acta, vol. 1819, Oct. 19, 2011, 97-103.
Os07g0225300 GenBank database accession No. BAF21127.1 Aug. 11, 2012.

* cited by examiner

Primary Examiner — Charles Logsdon

(57) ABSTRACT

The disclosure discloses isolated polynucleotides and polypeptides, and recombinant DNA constructs useful for conferring improved nitrogen use efficiency and drought tolerance; compositions (such as plants or seeds) comprising these recombinant DNA constructs; and methods utilizing these recombinant DNA constructs. The recombinant DNA constructs comprise a polynucleotide operably linked to a tissue specific or inducible promoter that is functional in a plant, wherein said polynucleotides encode NAC transcription factor polypeptides.

Figure 1:
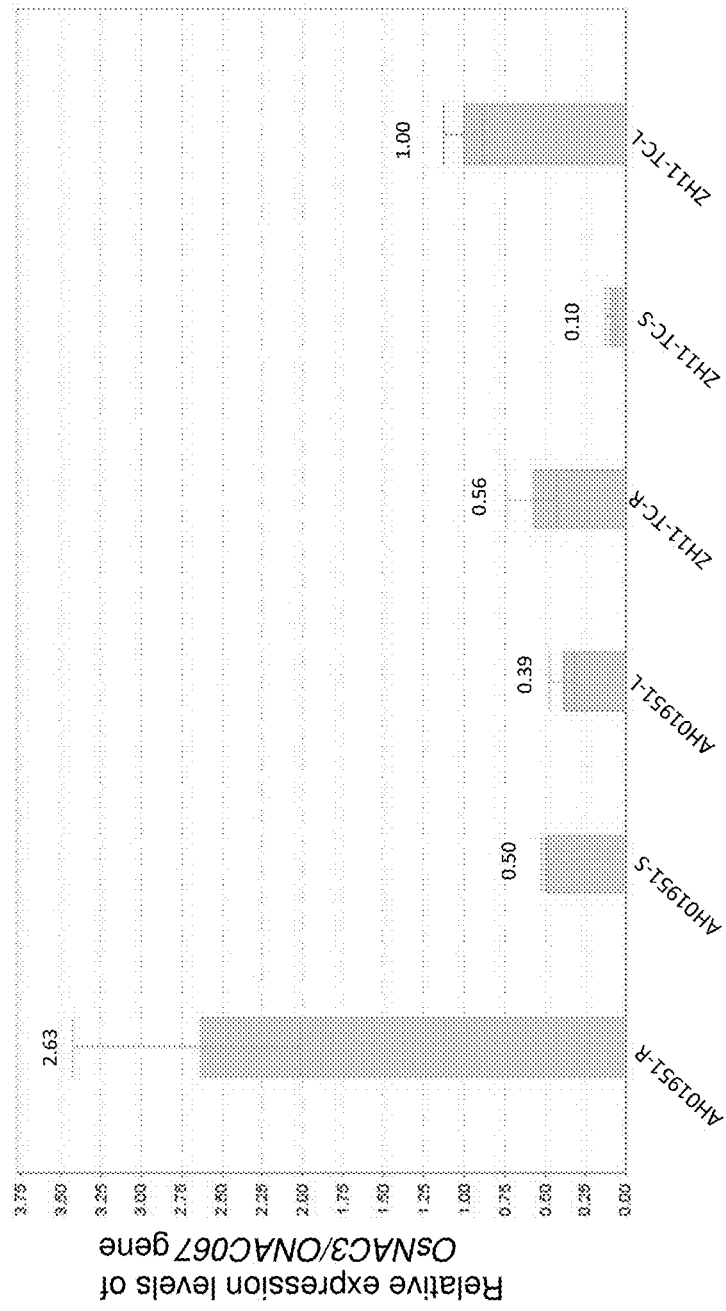

8 Claims, 4 Drawing Sheets
Specification includes a Sequence Listing.

US 10,662,435 B2

SEQUENCE LISTING

<160> NUMBER OF SEQ ID NOS: 11

<210> SEQ ID NO 1
<211> LENGTH: 923
<212> TYPE: DNA
<213> ORGANISM: Oryza sativa

<400> SEQUENCE: 1

```
agatctgaga ggtgtgggc tctctctcca tctttgtctc caaatcagat caccttttgc      60
ttttgacact gggttattct ttcagtgcct ataccaagaa aatctgaaga ttctgcgttg     120
tttacatgta aaacgttctg aacttgagaa aagtgaaaag cagtatctag tgtgaaattt     180
tgggtgctga ttctttcaag atgaaaggag ccttagatag tggaggcatc tggaagctgc     240
agcttccata tctggtaact tgatgctgcc tgcttgccta agttgctgtg ttaatcctag     300
tattatgtct gttaaaaata tgtgttgggc gacgctactc tcttttctga tttacatgtg     360
gaccaaccat gtggtaattg gagtcgatca gcatctgaaa cttgtttaga gtaataagtt     420
aattatgctt tttactgtgt tctctactgg tatacgaaag tttgacggtt cattcaacct     480
aacaagaagg aattttcggt tttcaattag ggaagatgta agtgtaaatt ccacatctag     540
tcgtgtatgg tctgcgccta tgctcactaa atccaaaagg tccatttgcc ttttttttt      600
```

```
tggattcatg tactcaagtg tctagaatcc cacgagggta aaagcctttc ttcccatgtt    660
tttacattgg acaaaaaggt tttcagactt ttagtgtaaa aagttgaaga atctgcagta    720
gtataagaga ttttatgcgc tgatttttat aaaagtata aggatcgata tttattgagg    780
aggcatatgt agatgcagcc ttggcgtaca tgccgtgctg tcaacggtga agactatatg    840
ctggtgtgtt tttccttcgt tccaactcgt tcgtttgcac cggccaggtt aacgaactac    900
taaaagaaag tggccctttt ttt                                           923

<210> SEQ ID NO 2
<211> LENGTH: 10952
<212> TYPE: DNA
<213> ORGANISM: Artificial Sequence
<220> FEATURE:
<223> OTHER INFORMATION: Nucleotide sequence of vector DP0005

<400> SEQUENCE: 2
gaattctcta gtcccgatct agtaacatag atgacaccgc gcgcgataat ttatcctagt     60
ttgcgcgcta tattttgttt tctatcgcgt attaaatgta taattgcggg actctaatca    120
taaaaaccca tctcataaat aacgtcatgc attacatgtt aattattaca tgcttaacgt    180
aattcaacag aaattatatg ataatcatcg caagaccggc aacaggattc aatcttaaga    240
aacgcggccg cttcagttgt ggcccagctt ggaggtcgac tcgcgaggat cctctagtcc    300
cgatctagta acatagatga caccgcgcgc gataatttat cctagtttgc gcgctatatt    360
ttgttttcta tcgcgtatta aatgtataat tgcgggactc taatcataaa aacccatctc    420
ataaataacg tcatgcatta catgttaatt attacatgct taacgtaatt caacagaaat    480
tatatgataa tcatcgcaag accggcaaca ggattcaatc ttaagaaacg cggccgcttc    540
agttgtggcc cagcttggag ggggcggcgt cgcagtagcg cccacggcg gcctcgtact    600 gcttgtagca cttgcccttc tccacctcct ccaggatctc gatgcggtgg tcctcgaagt    660
ggaagccggg catcttcagg gcggaggcgg gcttcttgga gcggtaggtg gtgtgcaggt    720
ggcaggtcag gtggcgaccg ccggggcact ccagggccat cagggactgg ccgcgcagca    780
cgccgtccac ctcgtacacg atctcggtgg agggctccca gcggccggcc ttgttctgca    840
tcacggggcc gtcggcgggg aagttgttgc ccaggatctt caccttgtac accaggcagt    900
cgccgtccag ggaggtgtcc tggtgggcgg tcaggaagcc gccgtcctcg taggtggtgg    960
tgcgctccca ggtgaagccc tcggggaggg actgcttgaa gtagtcgggg atgccggaca   1020
cgtacttgat gaaggccttg gagccgtaca tgcaggaggg gacaggatg tggaaggcga   1080 agggcagggg gccgccctcg atcacctcga tcttcatctc ctgggtgccc tccaggggt    1140 tgccctcgcc cttgccggtg cacttgaagt agtggccgtt cacggtgccc tcgatggtgg   1200
tcctgaaggg catggtcttc ttcagcaaag aggccatggt ggcgaccggt accagatctc   1260
tgcagagaga tagatttgta gagagagact ggtgatttca gcgtgtcctc tccaaatgaa   1320
atgaacttcc ttatatagag gaagggtctt gcgaaggata gtgggattgt gcgtcatccc   1380
ttacgtcagt ggagatatca catcaatcca cttgctttga agacgtggtt ggaacgtctt   1440 cttttccac gatgctcctc gtgggtgggg gtccatcttt ggaccactg tcggcagagg    1500 catcttgaac gatagccttt cctttatcgc aatgatggca tttgtaggtg ccaccttcct   1560
tttctactgt ccttttgatg aagtgacaga tagctgggca atggaatccg aggaggtttc   1620
ccgatattac cctttgttga aaagtctcaa tagcccttg gtcttctgag actgtatctt   1680
```

```
tgatattctt ggagtagacg agagtgtcgt gctccaccat gttcacatca atccacttgc    1740
tttgaagacg tggttggaac gtcttctttt tccacgatgc tcctcgtggg tgggggtcca    1800
tctttgggac cactgtcggc agaggcatct tgaacgatag cctttccttt atcgcaatga    1860
tggcatttgt aggtgccacc ttccttttct actgtccttt tgatgaagtg acagatagct    1920
gggcaatgga atccgaggag gtttcccgat attacccttt gttgaaaagt ctcaatagcc    1980
ctttggtctt ctgagactgt atctttgata ttcttggagt agacgagagt gtcgtgctcc    2040
accatgttgc caagctgctc taagcttggc actggccgtc gttttacaac gtcgtgactg    2100
ggaaaaccct ggcgttaccc aacttaatcg ccttgcagca catccccctt tcgccagctg    2160
gcgtaatagc gaagaggccc gcaccgatcg cccttcccaa cagttgcgca gcctgaatgg    2220
cgaatgctag agcagcttga gcttggatca gattgtcgtt actatcagtg tttgacagga    2280
tatattggcg ggtaaaccta agagaaaaga gcgtttatta gaataacgga tatttaaaag    2340
ggcgtgaaaa ggtttatccg ttcgtccatt tgtatgtgca tgccaaccac agggttcccc    2400
tcgggatcaa agtactttga tccaaccccct ccgctgctat agtgcagtcg gcttctgacg    2460
ttcagtgcag ccgtcttctg aaaacgacat gtcgcacaag tcctaagtta cgcgacaggc    2520
tgccgccctg cccttttcct ggcgttttct tgtcgcgtgt tttagtcgca taaagtagaa    2580
tacttgcgac tagaaccgga gacattacgc catgaacaag agcgccgccg ctggcctgct    2640
gggctatgcc cgcgtcagca ccgacgacca ggacttgacc aaccaacggg ccgaactgca    2700
cgcggccggc tgcaccaagc tgttttccga aagatcacc ggcaccaggc gcgaccgccc    2760
ggagctggcc aggatgcttg accacctacg ccctggcgac gttgtgacag tgaccaggct    2820
agaccgcctg gcccgcagca cccgcgacct actggacatt gccgagcgca tccaggaggc    2880
cggcgcgggc ctgcgtagcc tggcagagcc gtgggccgac accaccacgc cggccggccg    2940
catggtgttg accgtgttcg ccggcattgc cgagttcgag cgttccctaa tcatcgaccg    3000
cacccggagc gggcgcgagg ccgccaaggc ccgaggcgtg aagtttggcc ccgccctac    3060
cctcaccccg gcacagatcg cgcacgcccg cgagctgatc gaccaggaag gccgcaccgt    3120
gaaagaggcg gctgcactgc ttggcgtgca tcgctcgacc ctgtaccgcg cacttgagcg    3180
cagcgaggaa gtgacgccca ccgaggccag gcggcgcggt gccttccgtg aggacgcatt    3240
gaccgaggcc gacgccctgg cggccgccga gaatgaacgc caagaggaac aagcatgaaa    3300
ccgcaccagg acggccagga cgaaccgttt ttcattaccg aagagatcga ggcggagatg    3360
atcgcggccg ggtacgtgtt cgagccgccc gcgcacgtct caaccgtgcg gctgcatgaa    3420
atcctggccg gtttgtctga tgccaagctg gcggcctggc cggccagctt ggccgctgaa    3480
gaaaccgagc gccgccgtct aaaaaggtga tgtgtatttg agtaaaacag cttgcgtcat    3540
gcggtcgctg cgtatatgat gcgatgagta aataaacaaa tacgcaaggg gaacgcatga    3600
aggttatcgc tgtacttaac cagaaaggcg ggtcaggcaa gacgaccatc gcaacccatc    3660
tagcccgcgc cctgcaactc gccggggccg atgttctgtt agtcgattcc gatccccagg    3720
gcagtgcccg cgattgggcg gccgtgcggg aagatcaacc gctaaccgtt gtcggcatcg    3780
accgcccgac gattgaccgc gacgtgaagg ccatcggccg gcgcgacttc gtagtgatcg    3840
acggagcgcc ccaggcggcg gacttggctg tgtccgcgat caaggcagcc gacttcgtgc    3900
tgattccggt gcagccaagc ccttacgaca tatgggccac cgccgacctg gtggagctgg    3960
ttaagcagcg cattgaggtc acggatggaa ggctacaagc ggcctttgtc gtgtcgcggg    4020
cgatcaaagg cacgcgcatc ggcggtgagg ttgccgaggc gctggccggg tacgagctgc    4080
```

```
ccattcttga gtcccgtatc acgcagcgcg tgagctaccc aggcactgcc gccgccggca    4140
caaccgttct tgaatcagaa cccgagggcg acgctgcccg cgaggtccag cgctggccg     4200 ctgaaattaa atcaaaactc atttgagtta atgaggtaaa gagaaaatga gcaaaagcac    4260
aaacacgcta agtgccggcc gtccgagcgc acgcagcagc aaggctgcaa cgttggccag    4320
cctggcagac acgccagcca tgaagcgggt caactttcag ttgccggcgg aggatcacac    4380
caagctgaag atgtacgcgg tacgccaagg caagaccatt accgagctgc tatctgaata    4440
catcgcgcag ctaccagagt aaatgagcaa atgaataaat gagtagatga attttagcgg    4500
ctaaaggagg cggcatggaa aatcaagaac aaccaggcac cgacgccgtg gaatgcccca    4560
tgtgtggagg aacgggcggt tggccaggcg taagcggctg ggttgtctgc cggccctgca    4620
atggcactgg aaccccaag cccgaggaat cggcgtgacg gtcgcaaacc atccggcccg     4680
gtacaaatcg gcgcggcgct gggtgatgac ctggtggaga agttgaaggc cgcgcaggcc    4740
gcccagcggc aacgcatcga ggcagaagca cgccccggtg aatcgtggca agcggccgct    4800
gatcgaatcc gcaaagaatc ccggcaaccg ccggcagccg gtgcgccgtc gattaggaag    4860
ccgcccaagg gcgacgagca accagatttt ttcgttccga tgctctatga cgtgggcacc    4920
cgcgatagtc gcagcatcat ggacgtggcc gttttccgtc tgtcgaagcg tgaccgacga    4980
gctggcgagg tgatccgcta cgagcttcca gacgggcacg tagaggtttc gcagggccg     5040 gccggcatgg ccagtgtgtg ggattacgac ctggtactga tggcggtttc ccatctaacc    5100
gaatccatga accgataccg ggaagggaag ggagacaagc ccggccgcgt gttccgtcca    5160
cacgttgcgg acgtactcaa gttctgccgg cgagccgatg gcggaaagca gaaagacgac    5220
ctggtagaaa cctgcattcg gttaaacacc acgcacgttg ccatgcagcg tacgaagaag    5280
gccaagaacg gccgcctggt gacggtatcc gagggtgaag ccttgattag ccgctacaag    5340
atcgtaaaga gcgaaaccgg gcggccgag tacatcgaga tcgagctagc tgattggatg     5400
taccgcgaga tcacagaagg caagaacccg gacgtgctga cggttcaccc cgattacttt    5460
ttgatcgatc ccggcatcgg ccgttttctc taccgcctgg cacgccgcgc gcaggcaag    5520 gcagaagcca gatggttgtt caagacgatc tacgaacgca gtggcagcgc cggagagttc    5580
aagaagttct gtttcaccgt gcgcaagctg atcgggtcaa atgacctgcc ggagtacgat    5640
ttgaaggagg aggcgggggca ggctggcccg atcctagtca tgcgctaccg caacctgatc    5700
gagggcgaag catccgccgg ttcctaatgt acggagcaga tgctagggca aattgcccta    5760
gcaggggaaa aaggtcgaaa aggtctcttt cctgtggata gcacgtacat tgggaaccca    5820
aagccgtaca ttgggaaccg gaaccgtac attgggaacc caaagccgta cattgggaac     5880
cggtcacaca tgtaagtgac tgatataaaa gagaaaaaag gcgattttc cgcctaaaac     5940 tctttaaaac ttattaaaac tcttaaaacc cgcctggcct gtgcataact gtctggccag    6000
cgcacagccg aagagctgca aaaagcgcct acccttcggt cgctgcgctc cctacgcccc    6060
gccgcttcgc gtcggcctat cgcggccgct ggccgctcaa aaatggctgg cctacggcca    6120
ggcaatctac cagggcgcgg acaagccgcg ccgtcgccac tcgaccgccg gcgcccacat    6180
caaggcaccc tgcctcgcgc gtttcggtga tgacggtgaa aacctctgac acatgcagct    6240
cccggagacg gtcacagctt gtctgtaagc ggatgccggg agcagacaag cccgtcaggg    6300
cgcgtcagcg ggtgttggcg ggtgtcgggg cgcagccatg acccagtcac gtagcgatag    6360
cggagtgtat actggcttaa ctatgcggca tcagagcaga ttgtactgag agtgcaccat    6420
```

```
atgcggtgtg aaataccgca cagatgcgta aggagaaaat accgcatcag gcgctcttcc     6480
gcttcctcgc tcactgactc gctgcgctcg gtcgttcggc tgcggcgagc ggtatcagct     6540
cactcaaagg cggtaatacg gttatccaca gaatcagggg ataacgcagg aaagaacatg     6600
tgagcaaaag gccagcaaaa ggccaggaac cgtaaaaagg ccgcgttgct ggcgtttttc     6660
cataggctcc gcccccctga cgagcatcac aaaaatcgac gctcaagtca gaggtggcga     6720
aacccgacag gactataaag ataccaggcg tttccccctg gaagctccct cgtgcgctct     6780
cctgttccga ccctgccgct taccggatac ctgtccgcct ttctcccttc gggaagcgtg     6840
gcgctttctc atagctcacg ctgtaggtat ctcagttcgg tgtaggtcgt tcgctccaag     6900
ctgggctgtg tgcacgaacc ccccgttcag cccgaccgct gcgccttatc cggtaactat     6960
cgtcttgagt ccaacccggt aagacacgac ttatcgccac tggcagcagc cactggtaac     7020
aggattagca gagcgaggta tgtaggcggt gctacagagt tcttgaagtg gtggcctaac     7080
tacggctaca ctagaaggac agtatttggt atctgcgctc tgctgaagcc agttaccttc     7140
ggaaaaagag ttggtagctc ttgatccggc aaacaaacca ccgctggtag cggtggtttt     7200
tttgtttgca agcagcagat tacgcgcaga aaaaaggat ctcaagaaga tcctttgatc     7260
ttttctacgg ggtctgacgc tcagtggaac gaaaactcac gttaagggat tttggtcatg     7320
cattctaggt actaaaacaa ttcatccagt aaaatataat attttatttt ctcccaatca     7380
ggcttgatcc ccagtaagtc aaaaaatagc tcgacatact gttcttcccc gatatcctcc     7440
ctgatcgacc ggacgcagaa ggcaatgtca taccacttgt ccgccctgcc gcttctccca     7500
agatcaataa agccacttac tttgccatct ttcacaaaga tgttgctgtc tcccaggtcg     7560
ccgtgggaaa agacaagttc ctcttcgggc ttttccgtct ttaaaaaatc atacagctcg     7620
cgcggatctt taaatggagt gtcttcttcc cagttttcgc aatccacatc ggccagatcg     7680
ttattcagta agtaatccaa ttcggctaag cggctgtcta agctattcgt atagggacaa     7740
tccgatatgt cgatggagtg aaagagcctg atgcactccg catacagctc gataatcttt     7800
tcagggcttt gttcatcttc atactcttcc gagcaaagga cgccatcggc ctcactcatg     7860
agcagattgc tccagccatc atgccgttca aagtgcagga cctttggaac aggcagcttt     7920
ccttccagcc atagcatcat gtcctttttcc cgttccacat cataggtggt ccctttatac     7980
cggctgtccg tcatttttaa atataggttt tcatttttctc ccaccagctt atataccttta    8040
gcaggagaca ttccttccgt atcttttacg cagcggtatt tttcgatcag ttttttcaat     8100
tccggtgata ttctcatttt agccatttat tatttccttc ctcttttcta cagtatttaa     8160
agataccccca agaagctaat tataacaaga cgaactccaa ttcactgttc cttgcattct     8220
aaaaccttaa ataccagaaa acagcttttt caaagttgtt ttcaaagttg gcgtataaca     8280
tagtatcgac ggagccgatt ttgaaaccgc ggtgatcaca ggcagcaacg ctctgtcatc     8340
gttacaatca acatgctacc ctccgcgaga tcatccgtgt ttcaaacccg gcagcttagt     8400
tgccgttctt ccgaatagca tcggtaacat gagcaaagtc tgccgcctta caacggctct     8460
cccgctgacg ccgtcccgga ctgatgggct gcctgtatcg agtggtgatt ttgtgccgag     8520
ctgccggtcg gggagctgtt ggctggctgg tggcaggata tattgtggtg taaacaaatt     8580
gacgcttaga caacttaata acacattgcg gacgttttta atgtactgaa ttaacgccga     8640
attaattcgg gggatctgga ttttagtact ggatttggt tttaggaatt agaaatttta      8700
ttgatagaag tattttacaa atacaaatac atactaaggg tttcttatat gctcaacaca     8760
tgagcgaaac cctataggaa ccctaattcc cttatctggg aactactcac acattattat     8820
```

```
ggagaaactc gagcttgtcg atcgacagat ccggtcggca tctactctat ttctttgccc    8880
tcggacgagt gctggggcgt cggtttccac tatcggcgag tacttctaca cagccatcgg    8940
tccagacggc cgcgcttctg cgggcgattt gtgtacgccc gacagtcccg gctccggatc    9000
ggacgattgc gtcgcatcga ccctgcgccc aagctgcatc atcgaaattg ccgtcaacca    9060
agctctgata gagttggtca agaccaatgc ggagcatata cgcccggagt cgtggcgatc    9120
ctgcaagctc cggatgcctc cgctcgaagt agcgcgtctg ctgctccata caagccaacc    9180
acggcctcca gaagaagatg ttggcgacct cgtattggga atccccgaac atcgcctcgc    9240
tccagtcaat gaccgctgtt atgcggccat tgtccgtcag gacattgttg gagccgaaat    9300
ccgcgtgcac gaggtgccgg acttcggggc agtcctcggc ccaaagcatc agctcatcga    9360
gagcctgcgc gacggacgca ctgacggtgt cgtccatcac agtttgccag tgatacacat    9420
ggggatcagc aatcgcgcat atgaaatcac gccatgtagt gtattgaccg attccttgcg    9480
gtccgaatgg gccgaacccg ctcgtctggc taagatcggc cgcagcgatc gcatccatag    9540
cctccgcgac cggttgtaga acagcgggca gttcggtttc aggcaggtct tgcaacgtga    9600
caccctgtgc acggcgggag atgcaatagg tcaggctctc gctaaactcc ccaatgtcaa    9660
gcacttccgg aatcgggagc gcggccgatg caaagtgccg ataaacataa cgatctttgt    9720
agaaaccatc ggcgcagcta tttacccgca ggacatatcc acgccctcct acatcgaagc    9780
tgaaagcacg agattcttcg ccctccgaga gctgcatcag gtcggagacg ctgtcgaact    9840
tttcgatcag aaacttctcg acagacgtcg cggtgagttc aggcttttc atatctcatt     9900
gccccccggg atctgcgaaa gctcgagaga gatagatttg tagagagaga ctggtgattt    9960
cagcgtgtcc tctccaaatg aaatgaactt ccttatatag aggaaggtct tgcgaaggat   10020
agtgggattg tgcgtcatcc cttacgtcag tggagatatc acatcaatcc acttgctttg   10080
aagacgtggt tggaacgtct tctttttcca cgatgctcct cgtgggtggg ggtccatctt   10140
tgggaccact gtcggcagag gcatcttgaa cgatagcctt tcctttatcg caatgatggc   10200
atttgtaggt gccaccttcc tttctactg tcctttgat gaagtgacag atagctgggc     10260
aatggaatcc gaggaggttt cccgatatta cccttgttg aaaagtctca atagccctt     10320
ggtcttctga gactgtatct ttgatattct tggagtagac gagagtgtcg tgctccacca   10380
tgttatcaca tcaatccact tgctttgaag acgtggttgg aacgtcttct ttttccacga   10440
tgctcctcgt gggtggggt ccatctttgg gaccactgtc ggcagaggca tcttgaacga    10500
tagccttcc tttatcgcaa tgatggcatt tgtaggtgcc accttccttt tctactgtcc    10560
ttttgatgaa gtgacagata gctgggcaat ggaatccgag gaggtttccc gatattaccc   10620
tttgttgaaa agtctcaata gccctttggt cttctgagac tgtatctttg atattcttgg   10680
agtagacgag agtgtcgtgc tccaccatgt tggcaagctg ctctagccaa tacgcaaacc   10740
gcctctcccc gcgcgttggc cgattcatta atgcagctgg cacgacaggt ttcccgactg   10800
gaaagcgggc agtgagcgca acgcaattaa tgtgagttag ctcactcatt aggcacccca   10860
ggctttacac tttatgcttc cggctcgtat gttgtgtgga attgtgagcg gataacaatt   10920
tcacacagga aacagctatg accatgatta cg                                  10952
```

<210> SEQ ID NO 3
<211> LENGTH: 979
<212> TYPE: DNA
<213> ORGANISM: Oryza sativa

<400> SEQUENCE: 3

```
ttccctcaag tcccaagatc gaacacctcg tgtccatggc ggcggcgaag cggcgagtgc        60
gcgacgcgga ggcggacctg aacctcccgc cgggcttccg cttccacccc accgacgagg       120
agctggtggc gcactacctc tgcccgcgcg ccgcggccg cgccgcccg gtccccatca        180
tcgccgagct cgacctctac cgccacgacc catgggacct ccccaccgc gccctcttcg        240
gccgccgcga gtggtacttc ttcaccccgc gcgaccgcaa gtaccccaac ggctcccgcc        300
ccaaccgcgc cgccgcctcg ggctactgga aggccaccgg cgccgacaag cccgtgctgc        360
acaacggcag gacggccggg atcaagaagg cgctcgtgtt ctaccacggc aagccccccc        420
gcggcgtcaa gacggagtgg atcatgcacg agtaccgcct cgccaagaag ggcggcgccg        480
ccgccgccgc gggcgcggc gcgctcaggc tggatgactg ggtgctgtgc ggctgtaca         540
acaagaagaa cgagtgggag aagatgcaga gcaggaagga ggaggaggag gccatggcgg        600
cggcgcagtc gtgggggag acgcggacgc cggagtcgga ggtcgtcgac agcgacgcgt         660
tcccggagat ggactactcg ctgccggcgg cgtcgttcga cgacgccctg ctgcccaagg        720
aggaggcgcg cgacgacgac tggctcatgg ggatgagcct cgacgacctc cagggcctcg        780
gctcgctgct gcaggccgac gacctctcca tgctcgcgcc ccgccggcg gcgaagacgg         840
agccgctcgg cgcgccattc ttctgagctc tctctctctc tctctctctc tctctgtgac        900
tgcaccactg tatataaatt cagagttttc agacatgttc agtattcaga gttctcaggc        960
aagttcagaa ttcagatgg                                                     979
```

<210> SEQ ID NO 4
<211> LENGTH: 831
<212> TYPE: DNA
<213> ORGANISM: Oryza sativa

<400> SEQUENCE: 4

```
atggcggcgg cgaagcggcg agtgcgcgac gcggaggcgg aacctgaacct cccgccgggc        60
ttccgcttcc accccaccga cgaggagctg gtggcgcact acctctgccc gcgcgccgcg       120
ggccgcgccg cccggtccc catcatcgcc gagctcgacc tctaccgcca cgacccatgg        180
gacctccccc accgcgccct cttcggccgc cgcgagtggt acttcttcac cccgcgcgac        240
cgcaagtacc ccaacggctc ccgccccaac cgcgccgccg cctcgggcta ctggaaggcc        300
accggcgccg acaagcccgt gctgcacaac ggcaggacgg ccgggatcaa gaaggcgctc       360
gtgttctacc acggcaagcc ccccgcggc gtcaagacgg agtggatcat gcacgagtac        420
cgcctcgcca agaagggcgg cgccgccgcc gccgcgggcg cggcgcgct caggctggat        480
gactgggtgc tgtgccggct gtacaacaag aagaacgagt gggagaagat gcagagcagg        540
aaggaggagg aggaggccat ggcggcggcg cagtcgtggg gggagacgcg gacgccggag        600
tcggaggtcg tcgacagcga cgcgttcccg gagatggact actcgctgcc ggcggcgtcg        660
ttcgacgacg ccctgctgcc caaggaggag gcgcgcgacg acgactggct catggggatg        720
agcctcgacg acctccaggg cctcggctcg ctgctgcagg ccgacgacct ctccatgctc        780
gcgccgccgc cggcggcgaa gacggagccg ctcggcgcgc cattcttctg a                 831
```

<210> SEQ ID NO 5
<211> LENGTH: 276
<212> TYPE: PRT
<213> ORGANISM: Oryza sativa

<400> SEQUENCE: 5

Met Ala Ala Ala Lys Arg Arg Val Arg Asp Ala Glu Ala Asp Leu Asn
1               5                   10                  15

Leu Pro Pro Gly Phe Arg Phe His Pro Thr Asp Glu Glu Leu Val Ala
            20                  25                  30

His Tyr Leu Cys Pro Arg Ala Ala Gly Arg Ala Ala Pro Val Pro Ile
        35                  40                  45

Ile Ala Glu Leu Asp Leu Tyr Arg His Asp Pro Trp Asp Leu Pro His
    50                  55                  60

Arg Ala Leu Phe Gly Arg Arg Glu Trp Tyr Phe Phe Thr Pro Arg Asp
65              70                  75                  80

Arg Lys Tyr Pro Asn Gly Ser Arg Pro Asn Arg Ala Ala Ala Ser Gly
                85                  90                  95

Tyr Trp Lys Ala Thr Gly Ala Asp Lys Pro Val Leu His Asn Gly Arg
            100                 105                 110

Thr Ala Gly Ile Lys Lys Ala Leu Val Phe Tyr His Gly Lys Pro Pro
        115                 120                 125

Arg Gly Val Lys Thr Glu Trp Ile Met His Glu Tyr Arg Leu Ala Lys
    130                 135                 140

Lys Gly Gly Ala Ala Ala Ala Gly Ala Gly Ala Leu Arg Leu Asp
145             150                 155                 160

Asp Trp Val Leu Cys Arg Leu Tyr Asn Lys Lys Asn Glu Trp Glu Lys
                165                 170                 175

Met Gln Ser Arg Lys Glu Glu Glu Ala Met Ala Ala Gln Ser
            180                 185                 190

Trp Gly Glu Thr Arg Thr Pro Glu Ser Glu Val Val Asp Ser Asp Ala
        195                 200                 205

Phe Pro Glu Met Asp Tyr Ser Leu Pro Ala Ala Ser Phe Asp Ala
    210                 215                 220

Leu Leu Pro Lys Glu Glu Ala Arg Asp Asp Asp Trp Leu Met Gly Met
225             230                 235                 240

Ser Leu Asp Asp Leu Gln Gly Leu Gly Ser Leu Leu Gln Ala Asp Asp
                245                 250                 255

Leu Ser Met Leu Ala Pro Pro Pro Ala Ala Lys Thr Glu Pro Leu Gly
            260                 265                 270

Ala Pro Phe Phe
        275

<210> SEQ ID NO 6
<211> LENGTH: 1000
<212> TYPE: DNA
<213> ORGANISM: Oryza sativa

<400> SEQUENCE: 6

```
gctatatgtg tacgtgatag tatatttaac aatgaatcaa atgatatgaa ataataaat      60
aattacttaa atattttgaa taagacgaat ggtcaaacac gtactaaaaa gtcaacggtg    120
tcaaacattt tgaaacggaa ggagtatatt cttttaactt tgtaatagtt atatataatt    180
gttcgtacct cgagtagtta tcataaaact attcaactat tcagaaaaaa aagagtacat    240
cttacgggag aaggccagcc aaaattagta catctcatgg tggatgccaa caatcaacaa    300
aacctaccaa tccacacatt attacacctg aaaacgatct ctagctctga ttaatttcaa    360
acttcgatta tggactagtc aacacttcct aatagcagtg aactttgatt tggccatatg    420
aatactccca actttcatac cgaaaatttt atcttcaaac tatgaattct aaggatattc    480
```

-continued

| | |
|---|---|
| ccttttaggc cgatcactag ttcccctttt tatttgcaga gaggaaacat gcaaatttga | 540 |
| tatagaaata tacaaggggg aagcatacat atgatgccta tctgccatcc caggtacatg | 600 |
| cctatctgcc aaaacaatca actaacctac caagtaccaa tcctcccata attgaacagc | 660 |
| tggaccagga aaaatcatca tctgtgtaca tcttaattga ccatattcat gcaagctctg | 720 |
| atcaagttgt gcaatgtcag tattatatta ctaagttagt agctagttag ttaaatatca | 780 |
| gtctaataaa tgtctaatca gagctgttag taggaaagag taggtcacca atctctcaaa | 840 |
| gacttataca agctagattc catcaccaca ctatataaac acacacacac ctgaacacca | 900 |
| gtcacacaac caaatcaagc tcagcttaat caatcacctc atcacacact cttagctaag | 960 |
| ctaagctaag ctaagctaga gctaatacaa gagcaaatta | 1000 |

<210> SEQ ID NO 7
<211> LENGTH: 1921
<212> TYPE: DNA
<213> ORGANISM: Artificial Sequence
<220> FEATURE:
<223> OTHER INFORMATION: Nucleotide sequence of DsRed expression
      cassette

<400> SEQUENCE: 7

| | |
|---|---|
| cgaagctggc cgctctagaa ctagtggatc tcgatgtgta gtctacgaga agggttaacc | 60 |
| gtctcttcgt gagaataacc gtggcctaaa aataagccga tgaggataaa taaaatgtgg | 120 |
| tggtacagta cttcaagagg tttactcatc aagaggatgc ttttccgatg agctctagta | 180 |
| gtacatcgga cctcacatac ctccattgtg gtgaaatatt ttgtgctcat ttagtgatgg | 240 |
| gtaaattttg tttatgtcac tctaggtttt gacatttcag ttttgccact cttaggtttt | 300 |
| gacaaataat ttccattccg cggcaaaagc aaaacaattt tattttactt ttaccactct | 360 |
| tagctttcac aatgtatcac aaatgccact ctagaaattc tgtttatgcc acagaatgtg | 420 |
| aaaaaaaaca ctcacttatt tgaagccaag gtgttcatgg catggaaatg tgacataaag | 480 |
| taacgttcgt gtataagaaa aaattgtact cctcgtaaca agagacggaa acatcatgag | 540 |
| acaatcgcgt ttggaaggct ttgcatcacc tttggatgat gcgcatgaat ggagtcgtct | 600 |
| gcttgctagc cttcgcctac cgcccactga gtccgggcgg caactaccat cggcgaacga | 660 |
| cccagctgac ctctaccgac cggacttgaa tgcgctacct tcgtcagcga cgatggccgc | 720 |
| gtacgctggc gacgtgcccc cgcatgcatg gcggcacatg gcgagctcag accgtgcgtg | 780 |
| gctggctaca aatacgtacc ccgtgagtgc cctagctaga aacttacacc tgcaactgcg | 840 |
| agagcgagcg tgtgagtgta gccgagtaga tcctcgccac catggcctcc tccgagaacg | 900 |
| tcatcaccga gttcatgcgc ttcaaggtgc gcatggaggg caccgtgaac ggccacgagt | 960 |
| tcgagatcga gggcgagggc gagggccgcc ctacgagggg ccacaacacc gtgaagctga | 1020 |
| aggtgacgaa gggcggcccc ctgcccttcg cctgggacat cctgtccccc cagttccagt | 1080 |
| acggctccaa ggtgtacgtg aagcaccccg ccgacatccc cgactacaag aagctgtcct | 1140 |
| tccccgaggg cttcaagtgg gagcgcgtga tgaacttcga ggacggcggc gtggcgaccg | 1200 |
| tgacccagga ctcctcccctg caggacggct gcttcatcta caaggtgaag ttcatcggcg | 1260 |
| tgaacttccc ctccgacggc cccgtgatgc agaagaagac catgggctgg gaggcctcca | 1320 |
| ccgagcgcct gtaccccgc gacggcgtgc tgaagggcga acccacaag gccctgaagc | 1380 |
| tgaaggacgg cggccactac ctggtggagt tcaagtccat ctacatggcc aagaagcccg | 1440 |
| tgcagctgcc cggctactac tacgtggacg ccaagctgga catcacctcc cacaacgagg | 1500 |

```
actacaccat cgtggagcag tacgagcgca ccgagggccg ccaccacctg ttcctgtagc    1560
ggcccatgga tattcgaacg cgtaggtacc acatggttaa cctagacttg tccatcttct    1620
ggattggcca acttaattaa tgtatgaaat aaaaggatgc acacatagtg acatgctaat    1680
cactataatg tgggcatcaa agttgtgtgt tatgtgtaat tactagttat ctgaataaaa    1740
gagaaagaga tcatccatat ttcttatcct aaatgaatgt cacgtgtctt tataattctt    1800
tgatgaacca gatgcatttc attaaccaaa tccatataca tataaatatt aatcatatat    1860
aattaatatc aattgggtta gcaaaacaaa tctagtctag gtgtgttttg cgaatgcggc    1920
c                                                                   1921

<210> SEQ ID NO 8
<211> LENGTH: 26
<212> TYPE: DNA
<213> ORGANISM: Artificial Sequence
<220> FEATURE:
<223> OTHER INFORMATION: Forward primer for cloning cDNA of
      OsNAC3/ONAC067

<400> SEQUENCE: 8
ttccctcaag tcccaagatc gaacac                                          26

<210> SEQ ID NO 9
<211> LENGTH: 26
<212> TYPE: DNA
<213> ORGANISM: Artificial Sequence
<220> FEATURE:
<223> OTHER INFORMATION: Reverse primer for cloning cDNA of
      OsNAC3/ONAC067

<400> SEQUENCE: 9
ccatctgaat tctgaacttg cctgag                                          26

<210> SEQ ID NO 10
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsNAC3/ONAC067

<400> SEQUENCE: 10
gcagagcagg aaggaggag                                                  19

<210> SEQ ID NO 11
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsNAC3/ONAC067

<400> SEQUENCE: 11
catccccatg agccagtc                                                   18
```

PLANTS HAVING ALTERED AGRONOMIC CHARACTERISTICS UNDER ABIOTIC STRESS CONDITIONS AND RELATED CONSTRUCTS AND METHODS INVOLVING GENES ENCODING NAC3/ONAC067 POLYPEPTIDES

FIELD

The field of the disclosure relates to plant breeding and genetics and, in particular, relates to recombinant DNA constructs useful in plants for conferring nitrogen use efficiency and/or tolerance to nitrogen limiting conditions, and for improving drought tolerance.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, nitrogen, temperature extremes, and synthetic chemicals such as herbicides.

Abiotic stresses such as drought, high salinity and deficiency of nutrient elements adversely affect the growth and productivity of plants including crops, which significantly limit crop production worldwide. Cumulatively, these factors are estimated to be responsible for an average 70% reduction in agricultural production. Plants are sessile and have to adjust to the prevailing environmental conditions of their surroundings. This has led to their development of a great plasticity in gene regulation, morphogenesis, and metabolism. Adaptation and defense strategies involve the activation of genes encoding proteins important in the acclimation or defense towards the different stressors.

Drought (insufficient available water) is one of the major abiotic stresses that limit crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) Curr. Opin. Plant Biol. 9:189-195; Wang, W., et al. (2003) Planta 218:1-14; Vinocur, B., and Altman, A. (2005) Curr. Opin. Biotechnol. 16:123-132; Chaves, M. M., and Oliveira, M. M. (2004) J. Exp. Bot. 55:2365-2384; Shinozaki, K., et al. (2003) Curr. Opin. Plant Biol. 6:410-417; Yamaguchi-Shinozaki, K., and Shinozaki, K. (2005) Trends Plant Sci. 10:88-94), it remains a major challenge in biology to understand the basic biochemical and molecular mechanisms for drought stress perception, signal transduction and tolerance. Genetic research has shown that drought tolerance is a quantitative trait, controlled by many genes. Molecular marker-assisted breeding has led to improved drought tolerance in crops. However, marker accuracy and breeding efficiency remain problematic (Ashraf M. (2010) Biotechnol. Adv. 28:169-183). Transgenic approaches to engineering drought tolerance in crops have made progress (Vinocur B. and Altman A. (2005) Curr. Opin. Biotechnol. 16:123-132; Lawlor D W. (2013) J. Exp. Bot. 64:83-108).

The absorption of nitrogen by plants plays an important role in their growth (Gallais et al., J. Exp. Bot. 55(396):295-306 (2004)). Plants synthesize amino acids from inorganic nitrogen in the environment. Consequently, nitrogen fertilization has been a powerful tool for increasing the yield of cultivated plants, such as rice, maize and soybean. Lack of sufficient plant available nitrogen for optimum growth and development may be considered as an abiotic stress. In order to avoid pollution by nitrates and to maintain a sufficient profit margin, today farmers desire to reduce the use of nitrogen fertilizer. If a plant variety has increased nitrogen assimilation capacity, it would also be expected to have increased growth and yield. In summary, plant varieties that have better nitrogen use efficiency (NUE) are desirable.

Activation tagging can be utilized to identify genes with the ability to affect a trait. This approach has been used in the model plant species Arabidopsis thaliana (Weigel et al., Plant Physiol. 122:1003-1013 (2000)). Insertions of transcriptional enhancer elements can dominantly activate and/or elevate the expression of nearby endogenous genes. This method can be used to identify genes of interest for a particular trait (e.g. nitrogen use efficiency in a plant, drought tolerance in plant), genes that when placed in an organism as a transgene, can alter that trait.

OsNAC3/ONAC067 is a NAC transcription factor which appears to be widespread in plants. Extensive investigation aided by the availability of several complete plant genomic sequences has identified 117 NAC genes in Arabidopsis, 151 in rice (Nuruzzaman et al., frontier in microbiology. 248:1-16 (2013)). The functions of this gene family are being studied broadly.

SUMMARY

The following embodiments are among those encompassed by the disclosure:

In one embodiment, the present disclosure includes an isolated polynucleotide enhancing nitrogen stress tolerance and drought tolerance in plant through over-expression, comprising: (a) a polynucleotide with nucleotide sequence of at least 85% sequence identity to SEQ ID NO: 3; (b) a polynucleotide with nucleotide sequence of at least 85% sequence identity to SEQ ID NO: 4; (c) a polynucleotide encoding a polypeptide with amino acid sequence of at least 90% sequence identity to SEQ ID NO: 5; or (d) the full complement of the nucleotide sequence of (a), (b) or (c). The nucleotide sequence comprises SEQ ID NO: 3 or SEQ ID NO: 4 and the amino acid sequence of the polypeptide comprises SEQ ID NO: 5.

In another embodiment, the present disclosure includes a recombinant DNA construct comprising the isolated polynucleotide operably linked to at least one regulatory sequence, wherein the polynucleotide comprises (a) a polynucleotide with nucleotide sequence of at least 85% sequence identity to SEQ ID NO: 3 or SEQ ID NO: 4; (b) a polynucleotide encoding a polypeptide with amino acid sequence of at least 90% sequence identity to SEQ ID NO: 5; or (c) the full complement of the nucleotide sequence of (a) or (b); the at least one regulatory sequence is a promoter functional in a plant.

In another embodiment, the said promoter is a tissue-specific promoter, further it may be a root-specific promoter with the nucleotide sequence shown in SEQ ID NO: 6.

In another embodiment, the present disclosure includes a plant or seed comprising a recombinant DNA construct comprising the polynucleotide operably linked to at least one regulatory sequence, wherein the polynucleotide comprises (a) a polynucleotide with nucleotide sequence of at least 85% sequence identity to SEQ ID NO: 3 or SEQ ID NO: 4; (b) a polynucleotide encoding a polypeptide with amino acid sequence of at least 90% sequence identity to SEQ ID NO: 5; or (c) the full complement of the nucleotide sequence of (a) or (b); the at least one regulatory sequence is a promoter functional in a plant.

In another embodiment, the present disclosure includes a plant comprising in its genome a recombinant DNA construct comprising a polynucleotide operably linked to at least one regulatory element, wherein the polynucleotide comprises (a) a polynucleotide with nucleotide sequence of at least 85% sequence identity to SEQ ID NO: 3 or SEQ ID NO: 4; (b) a polynucleotide encoding a polypeptide with amino acid sequence of at least 90% sequence identity to SEQ ID NO: 5; or (c) the full complement of the nucleotide sequence of (a) or (b); the at least one regulatory sequence is a promoter functional in a plant; the said plant exhibits improved nitrogen use efficiency (NUE) and/or exhibits enhanced drought tolerance when compared to a control plant. The said promoter is a tissue-specific promoter, further it may be a root-specific promoter with the nucleotide sequence shown in SEQ ID NO: 6.

In another embodiment, the present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, methods are provided for increasing nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 5; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased nitrogen stress tolerance or NUE when compared to a control plant not comprising the recombinant DNA construct.

In another embodiment, method are provided for evaluating nitrogen stress tolerance or NUE in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity when compared to SEQ ID NO: 5; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for nitrogen stress tolerance or NUE compared to a control plant not comprising the recombinant DNA construct.

In another embodiment, methods are provided for increasing drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity compared to SEQ ID NO: 5; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant not comprising the recombinant DNA construct.

In another embodiment, methods are provided for evaluating drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity compared to SEQ ID NO: 5; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to a control plant not comprising the recombinant DNA construct.

In another embodiment, methods are provided for determining an alteration of an agronomic characteristics in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity compared to SEQ ID NO: 5; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristics when compared to a control plant not comprising the recombinant DNA construct, wherein said determining step (d) comprises determining whether the transgenic plant exhibits an alteration of at least one agronomic characteristics when compared, under nitrogen limiting conditions and/or water limited conditions, to a control plant not comprising the recombinant DNA construct.

In another embodiment, the present disclosure concerns a recombinant DNA construct comprising any of the isolated polynucleotides of the present disclosure operably linked to at least one regulatory sequence, and a cell, a plant, and a seed comprising the recombinant DNA construct. The cell may be eukaryotic, e.g., a yeast, insect or plant cell, or prokaryotic, e.g., a bacterium.

BRIEF DESCRIPTION OF THE DRAWINGS AND SEQUENCE LISTINGS

The disclosure can be more fully understood from the following detailed description and the accompanying drawings and Sequence Listing which form a part of this application.

FIG. 1 shows the activated expression levels of OsNAC3/ONAC067 gene in different tissues of line AH01951 plants as revealed by real-time RT-PCR analyses using control. ZH11-TC, Zhonghua 11 from tissue culture without a construct; labeled to indicate source as R, roots; S, stems; L, leaves. The numbers on top of the columns are the fold-changes compared to the control leaves.

Figure 2A:
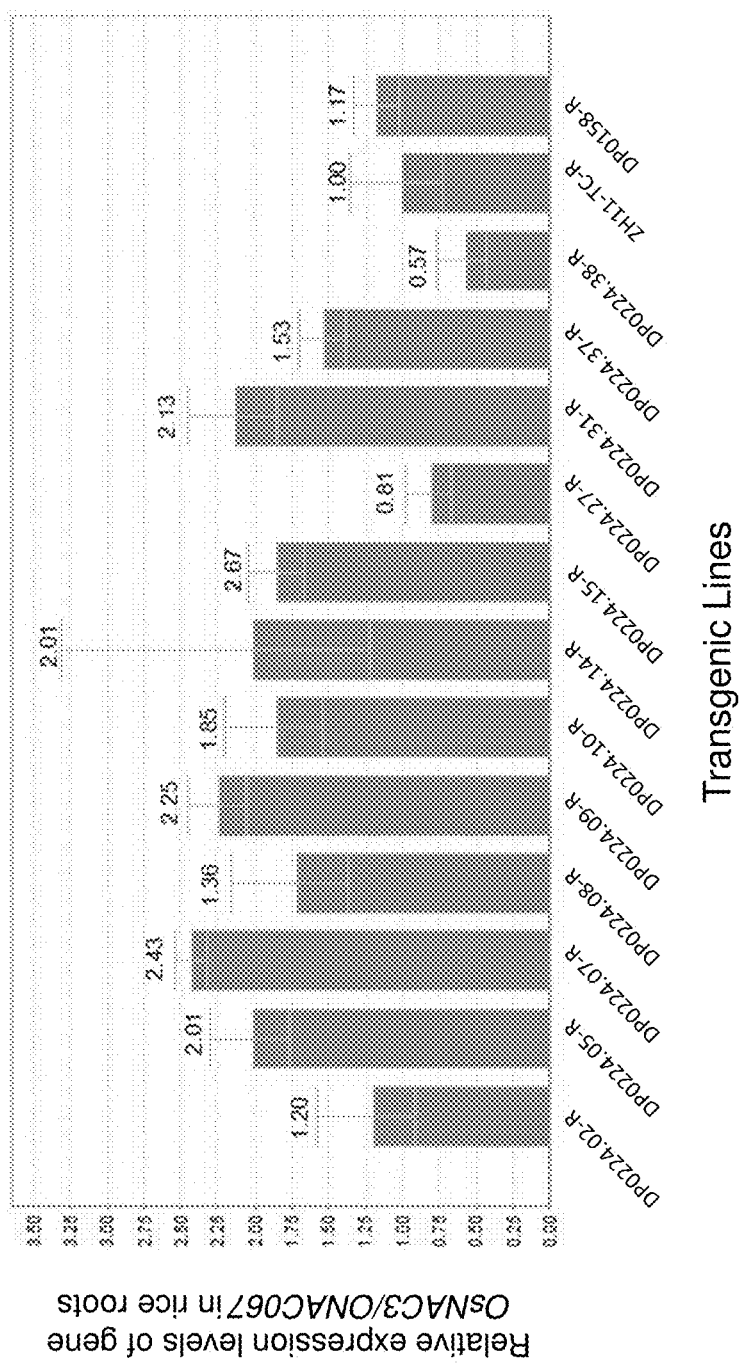
Figure 2B:
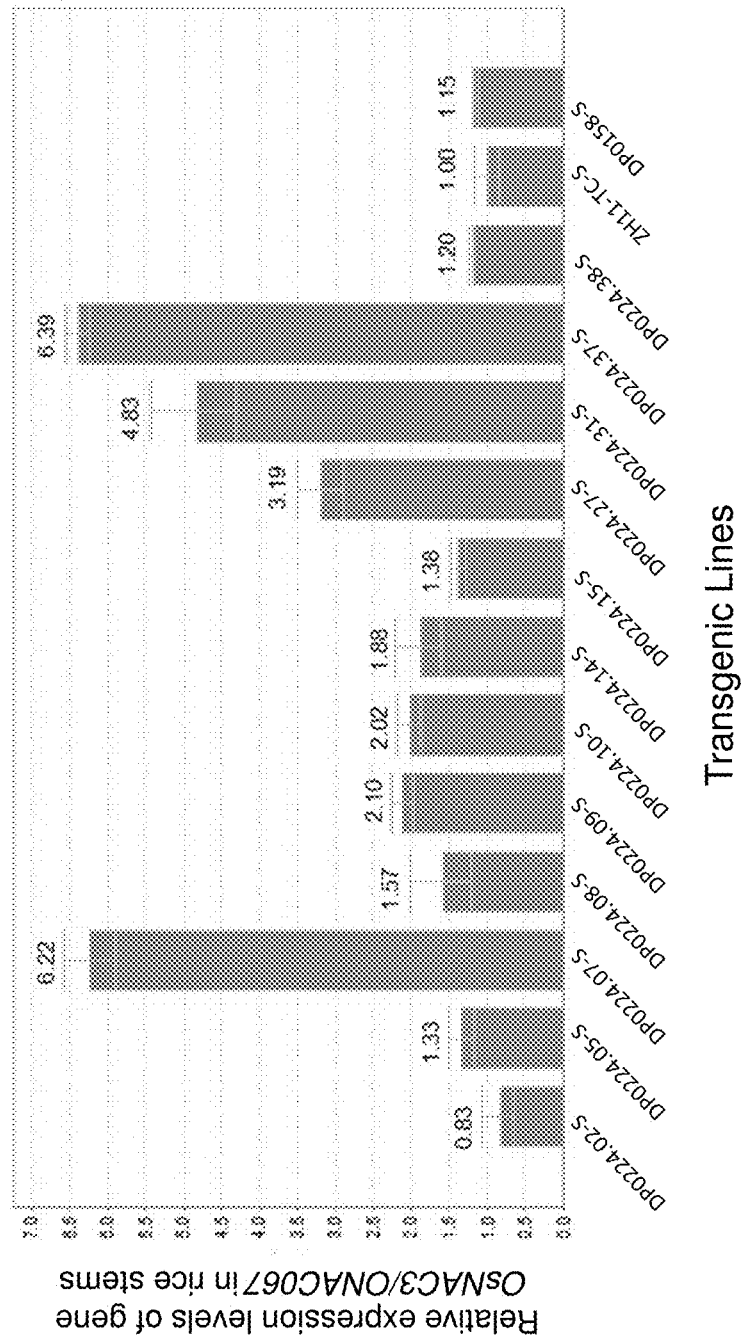
Figure 2C:
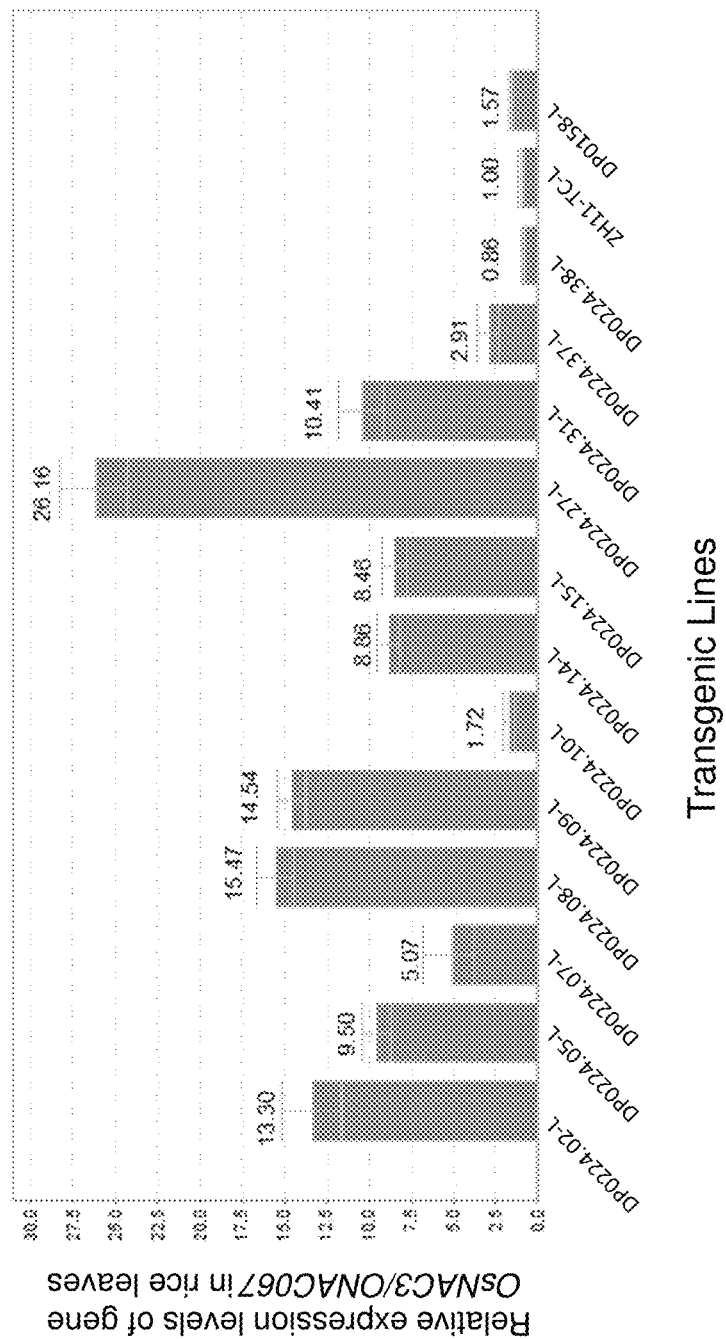

FIG. 2 provides OsNAC3/ONAC067 transgene expression levels in separate transgenic rice lines compared to control (ZH11-TC) by real-time RT-PCR analyses. The base level of expression in ZH11-TC was set at 1.00, and the expression levels in other OsNAC3/ONAC067 transgenic lines are shown as fold-increases compared to control. A. OsNAC3/ONAC067 transgene expression levels in roots; B. OsNAC3/ONAC067 transgene expression levels in stems; and C. OsNAC3/ONAC067 transgene expression levels in leaves.

Table 1. SEQ ID NOs for nucleotide and amino acid sequences provided in the sequence listing Table 2. Modified Hoagland's nutrient solution Table 3. Low nitrogen tolerance assays of AH01951 rice at $T_2$ generation under greenhouse conditions Table 4. Field low nitrogen tolerance assays of AH01951 rice at $T_2$ generation Table 5. PCR reaction mixture for cloning OsNAC3/ONAC067 gene Table 6. PCR cycle conditions for OsNAC3/ONAC067 gene Table 7. Low nitrogen tolerance assay of OsNAC3/ONAC067 transgenic rice plants under greenhouse low nitrogen conditions ($1^{st}$ experiment)

Table 8. Low nitrogen tolerance assay of OsNAC3/ONAC067 transgenic rice plants under greenhouse low nitrogen conditions ($2^{nd}$ experiment)

Table 9. Low nitrogen tolerance assay of OsNAC3/ONAC067 transgenic rice plants under greenhouse low nitrogen conditions ($3^{rd}$ experiment, ZH11-TC was used as control)

Table 10. Low nitrogen tolerance assay of OsNAC3/ONAC067 transgenic rice plants under greenhouse low nitrogen conditions ($3^{rd}$ experiment, DP0158 was used as control)

Table 11. Chlorate sensitive assay of OsNAC3/ONAC067 transgenic rice seedlings at the transgenic line level ($1^{st}$ experiment)

Table 12. Chlorate sensitive assay of OsNAC3/ONAC067 transgenic rice seedlings at the transgenic line level ($2^{nd}$ experiment)

Table 13. Grain yield analysis of OsNAC3/ONAC067 transgenic rice under low nitrogen conditions during the whole growth period Table 14. Biomass analysis of OsNAC3/ONAC067 transgenic rice under low nitrogen conditions during the whole growth period Table 15. Stem thickness analysis of OsNAC3/ONAC067 transgenic rice under low nitrogen conditions Table 16. Plant height analysis of OsNAC3/ONAC067 transgenic rice under low nitrogen conditions during the whole growth period Table 17. Drought tolerance assay of OsNAC3/ONAC067 transgenic rice plants under greenhouse drought conditions (at construct level)

Table 18. Drought tolerance assay of OsNAC3/ONAC067 transgenic rice plants under greenhouse drought conditions (at transgenic line level)

Table 19. Paraquat tolerance assay of OsNAC3/ONAC067 transgenic rice seedlings at transgenic lines level ($1^{st}$ experiment)

Table 20. Paraquat tolerance assay of OsNAC3/ONAC067 transgenic rice seedlings at transgenic lines level ($2^{nd}$ experiment)

Table 21. Paraquat tolerance assay of OsNAC3/ONAC067 transgenic rice seedlings at transgenic lines level ($3^{rd}$ experiment)

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Oryza sativa | T-DNA flanking sequence in AH01951 (RB) | 1 | n/a |
| Artificial | DP0005 vector | 2 | n/a |
| Oryza sativa | OsNAC3/ONAC067 | 3, 4 | 5 |
| Oryza sativa | KT630P | 6 | n/a |
| Artificial | DsRED expression cassette | 7 | n/a |
| Artificial | Primers | 8-11 | n/a |

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of the flanking sequence of the inserted T-DNA at the right border in AH01951 mutant.

SEQ ID NO: 2 is the nucleotide sequence of vector DP0005.

SEQ ID NO: 3 is the nucleotide sequence of cDNA of OsNAC3/ONAC067 gene.

SEQ ID NO: 4 is the nucleotide sequence of CDS of OsNAC3/ONAC067 gene.

SEQ ID NO: 5 is the amino acid sequence of OsNAC3/ONAC067.

SEQ ID NO: 6 is the nucleotide sequence of a root-specific promoter KT630P.

SEQ ID NO: 7 is the nucleotide sequence of DsRed expression cassette.

SEQ ID NO: 8 is forward primer for cloning cDNA of OsNAC3/ONAC067.

SEQ ID NO: 9 is reverse primer for cloning cDNA of OsNAC3/ONAC067.

SEQ ID NO: 10 is forward primer for real-time RT-PCR analysis of OsNAC3/ONAC067.

SEQ ID NO: 11 is reverse primer for real-time RT-PCR analysis of OsNAC3/ONAC067.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The term "OsNAC3/ONAC067" refers to a rice polypeptide that confers a low nitrogen tolerance, chlorate sensitive, drought tolerance and paraquat tolerance phenotype and is encoded by the rice gene locus LOC_Os07g12340.1. "NAC3/ONAC067 polypeptide" refers herein to the OsNAC3/ONAC067 polypeptide and its homologs from other organisms.

The OsNAC3/ONAC067 polypeptide (SEQ ID NO: 5) is encoded by the coding sequence (CDS) (SEQ ID NO: 4) or nucleotide sequence (SEQ ID NO: 3) at rice gene locus LOC_Os7g12340.1. This polypeptide is annotated as "NAC domain-containing protein 67, putative, expressed" in TIGR (the internet at rice.plantbiology.msu.edu/index.shtml), however does not have any prior assigned function.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristics of a plant or particular plant material or cell. In some instances, this characteristics is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristics" is a measurable parameter including but not limited to, greenness, yield, growth rate, biomass, fresh weight, dry weight at maturation, fruit yield, seed yield, total plant nitrogen content, fruit nitrogen content, seed nitrogen content, nitrogen content in vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, and ear length, early seedling vigor, and seedling emergence under low temperature stress.

"Harvest index" refers to the grain weight divided by the total plant weight.

Increased biomass can be measured, for example, as an increase in plant height, plant total leaf area, plant fresh weight, plant dry weight or plant grain yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products.

Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including nutrient deprivation and/or water deprivation, because larger roots may better reach or take up nutrients and/or water.

"Environmental conditions" refer to conditions under which the plant is grown, such as the availability of water, availability of nutrients (for example nitrogen), or the presence of insects or disease.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

The terms "nitrogen stress tolerance", "low nitrogen tolerance" and "nitrogen deficiency tolerance" are used interchangeably herein, which indicate a trait of a plant and refer to the ability of the plant to survive under nitrogen limiting conditions or low nitrogen conditions.

"Increased nitrogen stress tolerance" of a polypeptide indicates that over-expression of the polypeptide in a transgenic plant confers increased nitrogen stress tolerance of the transgenic plant relative to a reference or control plant.

"Increased nitrogen stress tolerance" of a plant is measured relative to a reference or control plant, reflects ability of the plant to survive and/or grow better under nitrogen limiting conditions, and means that the nitrogen stress tolerance of the plant is increased by any amount or measured when compared to the nitrogen stress tolerance of the reference or control plant.

A "nitrogen stress tolerant plant" is a plant that exhibits nitrogen stress tolerance. A nitrogen stress tolerant plant can be a plant that exhibits an increase in at least one agronomic characteristic relative to a control plant under nitrogen limiting conditions.

"NUE" is nitrogen utilization efficiency and refers to a plant's ability to utilize nitrogen in low or high levels of fertilizer. It reflects plant ability to uptake, assimilate, and/or otherwise utilize nitrogen.

Soil plant analyses development (SPAD) value is SPAD reading which is measured by SPAD-502 plus (a chlorophyll meter, made by KONICA MINOLTA).the SPAD value is relative content of leaf chlorophyll and an important indicator of plant health. Many studies indicated that a significant and positive correlation was observed between leaf nitrogen content and SPAD value (Swain D. K. and Sandip S. J. (2010) *Journal of Agronomy* 9 (2):38-44), and leaf SPAD value is used as index of nitrogen status diagnosis in crops (Cai H.-G. et al. (2010) *Acta metallurgica sinica* 16 (4):866-873).

The response and tolerance of rice plants to low nutrition stress is an integrated and comprehensive physiological and biochemical process. The tolerance of plants will be reflected in different aspect under different plant development phase and different stress conditions. The environment factors such as illumination and temperature are critical factors which effect rice growth, and the variation of these environment factors will influence the growth and development of rice plants. Researches demonstrated that low nitrogen treated rice plants display low chlorophyll content in leaf, deduced tiller number, or reduced biomass. In our experiment, the leaf color (which can be indicated by chlorophyll, SPAD value), plant fresh weight, and tiller number are measured, and the low nitrogen tolerance plants are selected by combining the three parameters.

"Chlorate" refers to a chemical compound containing chlorate anion, is salt of chloric acid. It is a nitrate analog which can be uptake by plant via same transport system as nitrate, and then converted by nitrate reductase to chlorite which is toxic and lead to plant damage, wither, dead. Potassium chlorate is used in this disclosure.

"Chlorate sensitivity" is a trait of plant, reflects the level of damage, even dead after chlorate uptake, transport or reduction when treated with chlorate solution, compared to a reference or control plant.

"Increased Chlorate sensitivity" of a plant is measured relative to a reference or control plant, and reflects higher ability of the plant to uptake, transport or reduce chlorate or nitrate than a reference or control plant in chlorate or nitrate solution. In general, chlorate sensitivity can be used as a marker of NUE. The more sensitive of plants are to chlorate, the higher NUE.

"Chlorate sensitive seedlings" are the damaged seedlings with phenotype of withered leaves in whole and without green leaf, and considered as dead after treated with chlorate solution.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Paraquat" (1,1-dimethyl-4,4-bipyridinium dichloride), is a foliar-applied and non-selective bipyridinium herbicides, and can mimic the environmental stresses as oxidative stress inducer at relatively low concentrations.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-TC, line null, and empty vector plants indicate control plants. ZH11-TC represents rice plants generated from tissue cultured Zhonghua 11, line null represents segregated null plants, and empty vector represents plants transformed with empty vector DP0158.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. The heterologous polynucleotide can be stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring improved nitrogen use efficiency and/or enhanced drought tolerance, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is preferably a NAC3/ONAC067. Over-expression of this polypeptide preferably increase plant low nitrogen tolerance activity and/or drought tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5. The polypeptide is preferably an NAC3/ONAC067 polypeptide.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO:3 or 4; or (ii) a full complement of the nucleic acid sequence of (i). Any of the foregoing isolated polynucleotides may be utilized in any recombinant DNA constructs of the present disclosure. The isolated polynucleotide preferably encodes a NAC3/ONAC067 protein. Over-expression of this polypeptide preferably increase plant low nitrogen tolerance activity and/or drought tolerance activity.

Recombinant DNA Constructs

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 3 or 4; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a NAC3/ONAC067 protein. This polypeptide preferably has low nitrogen tolerance activity and/or drought tolerance activity, and may be from, for example, Oryza sativa, Arabidopsis thaliana, Zea mays, Glycine max, Glycine tabacina, Glycine soja or Glycine tomentella.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing", as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on over-expression of a nucleic acid sequence having homology to a native mRNA, in the sense orientation, which results in the reduction of all RNA having homology to the over-expressed sequence (see Vaucheret et al., Plant J. 16:651-659 (1998); and Gura, Nature 404:804-808 (2000)).

Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., Nature 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., Science 294:853-858 (2001), Lagos-Quintana et al., Curr. Biol. 12:735-739 (2002); Lau et al., Science 294:858-862 (2001); Lee and Ambros, Science 294:862-864 (2001); Llave et al., Plant Cell 14:1605-1619 (2002); Mourelatos et al., Genes. Dev. 16:720-728 (2002); Park et al., Curr. Biol.

12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures.

MicroRNAs (miRNAs) appear to regulate target genes by binding to complementary sequences located in the transcripts produced by these genes. It seems likely that miRNAs can enter at least two pathways of target gene regulation: (1) translational inhibition; and (2) RNA cleavage. MicroRNAs entering the RNA cleavage pathway are analogous to the 21-25 nt short interfering RNAs (siRNAs) generated during RNA interference (RNAi) in animals and posttranscriptional gene silencing (PTGS) in plants, and likely are incorporated into an RNA-induced silencing complex (RISC) that is similar or identical to that seen for RNAi.

Regulatory Sequences:

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance nitrogen tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current disclosure include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228 (1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156 (2):155-166 (1995); NCBI GenBank Accession No. X80206)). Zag2 transcripts can be detected five days prior to pollination to seven to eight days after pollination ("DAP"), and directs expression in the carpel of developing female inflorescences and Ciml which is specific to the nucleus of developing maize kernels. Ciml transcript is detected four to five days before pollination to six to eight DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize led promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1B10 promoter (WO 2006/055487, published May 26, 2006), the CRWAQ81 (WO 2005/035770, published Apr. 21, 2005) and the maize ZRP2.47 promoter (NCBI Accession No. U38790; NCBI GI No. 1063664).

Recombinant DNA constructs of the present disclosure may also include other regulatory sequences including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

Any plant can be selected for the identification of regulatory sequences and genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristics (e.g., an increased agronomic characteristics optionally under nitrogen limiting conditions), or used in a breeding program to produce hybrid seed, which can be grown to produce plants that would exhibit such an altered agronomic characteristics. The seeds may be maize seeds, or rice seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A plant (for example, a rice, maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 5 and wherein said plant exhibits increased nitrogen stress tolerance and/or drought tolerance when compared to a control plant not comprising said recombinant DNA construct. The plant may further exhibit an alteration of at least one agronomic characteristic when compared to the control plant.

2. A plant (for example, a rice, maize or soybean plant) comprising in its genome a recombinant DNA construct comprising a polynucleotide operably linked to at least one regulatory sequence, wherein said polynucleotide encodes a NAC3/ONAC067 polypeptide, and wherein said plant exhibits increased nitrogen stress tolerance and/or drought tolerance when compared to a control plant not comprising said recombinant DNA construct. The plant may further exhibit an alteration of at least one agronomic characteristic when compared to the control plant. The NAC3/ONAC067 polypeptide may be from *Arabidopsis thaliana, Zea mays, Glycine max, Glycine tabacina, Glycine soja* or *Glycine tomentella*.

3. A plant (for example, a rice, maize or soybean plant) comprising in its genome a recombinant DNA construct comprising a polynucleotide operably linked to at least one regulatory sequence, wherein said polynucleotide encodes a NAC3/ONAC067 polypeptide, and wherein said plant exhibits an alteration of at least one agronomic characteristic under nitrogen limiting conditions or under water deficiency conditions when compared to a control plant not comprising said recombinant DNA construct. The NAC3/ONAC067 polypeptide may be from *Arabidopsis thaliana, Zea mays, Glycine max, Glycine tabacina, Glycine soja* or *Glycine tomentella*.

4. A plant (for example, a rice, maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 5, and wherein said plant exhibits an alteration of at least one agronomic characteristic under nitrogen limiting conditions or under water deficiency conditions when compared to a control plant not comprising said recombinant DNA construct.

5. Any progeny of the above plants in embodiment 1-4, any seeds of the above plants in embodiment 1-4, any seeds of progeny of the above plants in embodiment 1-4, and cells from any of the above plants in embodiment 1-4 and progeny thereof.

In any of the foregoing embodiment 1-5 or any other embodiments of the present disclosure, the recombinant DNA construct may comprises at least a promoter functional in a plant as a regulatory sequence.

In any of the foregoing embodiment 1-5 or any other embodiments of the present disclosure, the alteration of at least one agronomic characteristic is either an increase or decrease.

In any of the foregoing embodiment 1-5 or any other embodiments of the present disclosure, the at least one agronomic characteristic is may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear length, early seedling vigor, and seedling emergence under low temperature stress. For example, the alteration of at least one agronomic characteristic may be an increase in yield, greenness, or biomass.

In any of the foregoing embodiment 1-5 or any other embodiments of the present disclosure, the plant may exhibit the alteration of at least one agronomic characteristics when compared, under nitrogen stress conditions or under water deficiency conditions, to a control plant not comprising said recombinant DNA construct.

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, leaf color or leaf area size. Other techniques for evaluating such plants include measuring chlorophyll fluorescence, photosynthetic rates, root growth or gas exchange rates.

The examples below describe some representative protocols and techniques for simulating nitrogen limiting conditions and/or evaluating plants under such conditions, simulating drought conditions and/or evaluating drought tolerance; and simulating oxidative conditions.

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

SPAD value can be measured during low or high nitrogen condition in the field and greenhouse test by a chlorophyll meter. The SPAD value is a parameter indicating the plant health, and reflects plant nitrogen content by predicting the chlorophyll content. The plants with higher low nitrogen tolerance will have higher SPAD value compared to a control or reference plant.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

One of ordinary skill in the art would readily recognize a suitable control or reference plant to be utilized when assessing or measuring an agronomic characteristic or phenotype of a transgenic plant in any embodiment of the present disclosure in which a control is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct. There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristics or phenotype of a transgenic plant would not include a plant that had been previously selected, via mutagenesis or transformation, for the desired agronomic characteristic or phenotype.

Methods

Methods include but are not limited to methods for increasing nitrogen stress tolerance in a plant, methods for evaluating nitrogen stress tolerance in a plant, methods for increasing chlorate sensitive in a plant, methods for increasing drought tolerance in a plant, methods for evaluating drought tolerance in a plant, methods for increasing paraquat tolerance, methods for altering an agronomic characteristics in a plant, methods for determining an alteration of an agronomic characteristics in a plant, and methods for producing seed. The plant may be a monocotyledonous or dicotyledonous plant, for example, a rice, maize, *Arabidopsis*, soybean plant. The plant may also be sunflower, sorghum, canola, wheat, alfalfa, cotton, barley or millet. The seed may be a rice, maize, *Arabidopsis* or soybean seed, for example a maize hybrid seed or maize inbred seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing nitrogen stress tolerance and/or chlorate sensitivity in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 5; and (b) regenerating a transgenic plant from the regenerable plant cell after step (a), wherein the transgenic plant comprises in its genome the recombinant DNA construct and exhibits increased nitrogen stress tolerance and/or chlorate sensitivity when compared to a control plant not comprising the recombinant DNA construct. The method may further comprise (c) obtaining a progeny plant derived from the transgenic plant, wherein said progeny plant comprises in its genome the recombinant DNA construct and exhibits increased nitrogen tolerance and/or chlorate sensitivity when compared to a control plant not comprising the recombinant DNA construct.

A method of evaluating nitrogen stress tolerance and/or chlorate sensitivity in a plant, comprising (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 5; (b) regenerating a transgenic plant from the regenerable plant cell after step (a), wherein the transgenic plant comprises in its genome the recombinant DNA construct; and (c) evaluating the transgenic plant for nitrogen stress tolerance and/or chlorate sensitivity compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for nitrogen stress tolerance and/or chlorate sensitivity compared to a control plant not comprising the recombinant DNA construct.

A method of increasing drought tolerance and/or paraquat tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 5; (b) regenerating a transgenic plant from the regenerable plant cell after step (a), wherein the transgenic plant comprises in its genome the recombinant DNA construct and -exhibits increased drought tolerance and/or paraquat tolerance when compared to a control plant; and further (c) obtaining a progeny plant derived from transgenic plant, wherein said progeny plant comprises in its genome the recombinant DNA construct and exhibits increased drought tolerance and/or paraquat tolerance when compared to a control plant.

A method of evaluating drought tolerance and/or paraquat tolerance in a plant comprising (a) obtaining a transgenic plant, which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, to SEQ ID NO: 5; (b) obtaining a progeny plant derived from said transgenic plant, wherein the progeny plant comprises in its genome the recombinant DNA construct; and (c) evaluating the progeny plant for drought tolerance and/or paraquat tolerance compared to a control plant.

A method of determining an alteration of an agronomic characteristics in a plant, comprising (a) introducing into a regenerable plant cell a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 5; (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristics when compared, optionally under nitrogen limiting conditions and/or water deficiency conditions, to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristics when compared, optionally under nitrogen limiting conditions and/or water deficiency conditions, to a control plant not comprising the recombinant DNA construct.

A method of producing seed comprising any of the preceding methods, and further comprising obtaining seeds from said progeny plant, wherein said seeds comprise in their genome said recombinant DNA construct.

In any of the preceding methods or any other embodiments of methods of the present disclosure, the step of determining an alteration of an agronomic characteristics in a transgenic plant, if applicable, may comprise determining whether the transgenic plant exhibits an alteration of at least one agronomic characteristics when compared, under varying environmental conditions, to a control plant not comprising the recombinant DNA construct.

In any of the preceding methods or any other embodiments of methods of the present disclosure, the step of determining an alteration of an agronomic characteristics in a progeny plant, if applicable, may comprise determining whether the progeny plant exhibits an alteration of at least one agronomic characteristics when compared, under varying environmental conditions, to a control plant not comprising the recombinant DNA construct.

In any of the preceding methods or any other embodiments of methods of the present disclosure, in said introducing step said regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the at least one agronomic characteristics may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, whole plant amino acid content, vegetative tissue free amino acid content, fruit free amino acid content, seed free amino acid content, total plant protein content, fruit protein content, seed protein content, protein content in a vegetative tissue, drought tolerance, nitrogen uptake, resistance to root lodging, harvest index, stalk lodging, plant height, ear height, ear length, early seedling vigor, and seedling emergence under low temperature stress. The alteration of at least one agronomic characteristic may be an increase in yield, greenness, or biomass.

In any of the preceding methods or any other embodiments of methods of the present disclosure, the plant may exhibit the alteration of at least one agronomic characteristics when compared, under nitrogen stress conditions and/or water deficient conditions, to a control plant not comprising said recombinant DNA construct.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959):1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9:39; The CRISPR/Cas system allows targeted cleavage of genomic DNA guided by a customizable small noncoding RNA.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Creation of a Rice Population with an Activation-Tagging Construct

In this research, a binary construct that contains four multimerized enhancers elements derived from the Cauliflower Mosaic Virus 35S (CaMV 35S) promoter was used, and the rice activation tagging population was developed from Zhonghua 11 (*Oryza sativa* L.) which was transformed by *Agrobacteria*-mediated transformation method as described by Lin and Zhang ((2005) *Plant Cell Rep.* 23:540-547). Zhonghua 11 was cultivated by Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with *Agrobacteria* with the vector. The transgenic lines generated were developed and the transgenic seeds were harvested to form the rice activation tagging population.

Example 2

Seedling Screens to Identify Lines with Enhanced Nitrogen Use Efficiency (NUE) in Greenhouse Seedling screens for nitrogen use efficiency (NUE) are carried out in greenhouse. Two types of lamps are provided as light source, i.e. sodium lamp and metal halide lamp, the ratio is 1:1. Lamps provide the 16 h/8 h period of day/night, and are placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C.

The $T_2$ seeds which showed red color under green fluorescent light are used for NUE greenhouse screens except as otherwise specifically noted. Seeds are sterilized by 800 ppm carbendazol for 8 h at 32° C. and washed 3-5 times, then soaked in water for 16 h at 32° C., germinated for 18 h at 35-37° C. in an incubator. The germinated seeds are sowed in pot filled with vermiculite and then are evenly covered with wet vermiculite about 1 cm in depth. Then the pots were placed in one container and watered with pH5.2 tap water adjusted by 20% $H_2SO_4$, the water is changed every day. For each line to be tested, 6 uniform seedlings are planted, 2 plants are planted in one pot. In each tray, there are 21 mutant lines plus 1 positive control (Liutiaonuo), 1 negative control (Liaojing 294) and 1 transformed wild type control from tissue culture procedure. Three trays are placed in one container. When the seedlings grew to 3-leaf stage, water is replaced with modified Hoagland solution containing 0.75 mM nitrogen ($KNO_3$) as shown in Table 2. To make aerobic condition, the nutrition solution is drained off every Monday, Wednesday, and Friday for 2-3 h, and then new modified Hoagland containing low nitrogen solution is added. When the positive control plants differentiated tillers, SPAD value is measured by a SPAD meter (SPAD 502 Plus, made by KONICA MINOLTA) with three different positions of the second leaf from the top, and the SPAD value is the average of three readings; tiller (including the stem and all tillers) numbers are counted, the fresh weight of the seedling (cutting from the joint of root and stem) is measured by one percent of the balance. The data are statistically analyzed using SAS-software. After statistical analysis of these data (SPAD value, tiller number and fresh weight), the positive lines are selected by P≤0.05.

TABLE 2

Modified Hoagland's nutrient solution

| Molecular formula | Mass concentration (g/L) |
|---|---|
| $KH_2PO_4$ | 34.38 |
| $MgSO_4 \cdot 7H_2O$ | 246.50 |
| $CaCl_2 \cdot 2H_2O$ | 146.88 |
| KCl | 242.29 |
| $KNO_3$ | 101.00 |
| $Na_2SiO_3 \cdot 9H_2O$ | 142.00 |
| $H_3BO_3$ | 1.85 |
| $MnCl_2 \cdot 4H_2O$ | 1.98 |
| $ZnSO_4 \cdot 7H_2O$ | 2.87 |
| $CuSO_4 \cdot 5H_2O$ | 0.25 |
| $(NH_4)_6MoO_{24} \cdot 2H_2O$ | 0.24 |

TABLE 2-continued

Modified Hoagland's nutrient solution

| Molecular formula | Mass concentration (g/L) |
|---|---|
| EDTA-2Na | 7.45 |
| $FeSO_4 \cdot 7H2O$ | 5.57 |

The positive lines which passed the second screens are screened again using transformed wild type Zhonghua 11 as controls. Lines which passed the third screen are planted in greenhouse soil or in field (depending the seasons) for harvesting leaf materials and molecular cloning of the T-DNA-flanking sequences and candidate genes. In general, 20-30 g of fresh leaf tissues were harvested from 30 uniform seedlings of the same line, frozen in liquid nitrogen, and stored in −80° C. freezer.

Example 3

Field Low Nitrogen Screens of Mature Plants

Field low nitrogen screens are carried out in Beijing. Two nitrogen levels: N-0 (using fertilizer without nitrogen) and N-1 (using normal fertilizer at 180 kg Nitrogen/acre) are set in this assay. Seed germination and seedling culturing are performed as described in Example 2. At 3-leaf stage, the seedlings are transplanted into two testing fields, with 4 replicates and 10 plants per replicate for each tagged line, and the 4 replicates are planted in the same block. The wild type Zhonghua 11 plants which are from the tissue culture procedure, are nearby the tagged lines in the same block, and are used as controls in the statistical analysis.

The rice plants are managed by normal practice using pesticides, but applying phosphor fertilizer and potassium fertilizer for N-0 treatment testing field and normal fertilizers for N-1 testing field during the whole growth period.

At the end of the season, several representative plants of each tagged line are harvested from the middle of the row per line, the panicle weight per plant, panicle number per plant and grain yield per plant are measured. The grain yield data are statistically analyzed using mixed linear model by ASRemI program. Positive tagged lines are selected based on the analysis (P<0.1).

Example 4

Results for Line AH01951

Tiller number, SPAD value, and fresh weight were used as parameters of NUE or tolerance to the low nitrogen stress. As shown in Table 3, the tiller numbers of AH01951 and control plants were same; however the average SPAD value of AH01951 was significantly higher than that of ZH11-TC seedlings, indicating that AH01951 rice has low nitrogen tolerance compared to the control.

Then three rounds of screens were carried out to confirm the observations. As indicated in Table 3, the average SPAD value, or tiller number, or fresh weight of AH01951 rice plants was significantly higher than that of ZH-TC in the further screens. These results demonstrate that AH01951 plants have enhanced low nitrogen tolerance or enhanced NUE under greenhouse low nitrogen conditions.

TABLE 3

Low nitrogen tolerance assays of AH01951 rice at T₂ generation under greenhouse conditions

| ATL ID | Screening round | Tiller number | | | SPAD value | | | Fresh weight | | |
|---|---|---|---|---|---|---|---|---|---|---|
| | | Average tiller number | P value | P ≤ 0.05 | Average SPAD value | P value | P ≤ 0.05 | Average fresh weight | P value | P ≤ 0.05 |
| AH01951 | 1st | 1.0 | 1.000 | | 21.13 | 0.029 | Y | | | |
| ZH11-TC | | 1.0 | | | 11.73 | | | | | |
| AH01951 | 2nd | 2.3 | 0.000 | Y | 31.83 | 0.102 | | | | |
| ZH11-TC | | 1.2 | | | 22.25 | | | | | |
| AH01951 | 3rd | 1.3 | 0.386 | | 16.48 | 0.201 | | 1.767 | 0.018 | Y |
| ZH11-TC | | 1.5 | | | 16.05 | | | 1.317 | | |
| AH01951 | 4th | 2.6 | 0.000 | Y | 39.44 | 0.341 | | 5.088 | 0.000 | Y |
| ZH11-TC | | 1.3 | | | 38.23 | | | 3.306 | | |

Field low nitrogen assays were carried out in Beijing field as described in Example 3. Three parameters were measured after harvesting the rice plants. Under low nitrogen conditions, the panicle number per plant of AH01951 was significantly greater than that of ZH11-TC control (P value=0.011), its panicle weight per plant was equal to that of the ZH11-TC control, and its grain yield per plant was less than ZH11-TC without significant difference (Table 4). All of the three parameters of AH01951 line were better than that of ZH11-TC control under normal nitrogen conditions (N-1). These results indicate that AH01951 rice plants have better low nitrogen tolerance and had better yield under normal nitrogen conditions.

TABLE 4

Field low nitrogen tolerance assays of AH01951 rice at T₂ generation

| ATL ID | Treatment | Panicle number per plant | P value | Panicle weight per plant (g) | P value | Yield per plant (g) | P value |
|---|---|---|---|---|---|---|---|
| AH01951 | N-0 | 4.83 | 0.011 | 18.53 | 0.962 | 15.76 | 0.666 |
| ZH11-TC | | 3.68 | | 18.65 | | 16.70 | |
| AH01951 | N-1 | 7.86 | 0.634 | 35.56 | 0.228 | 30.71 | 0.417 |
| ZH11-TC | | 7.39 | | 32.00 | | 28.57 | |

In light of these results, further work was carried out to identify the gene(s) which contributed to the enhanced low nitrogen tolerance of Line AH01951.

Example 5

Identification of Activation-Tagged Genes

Genes flanking the T-DNA insertion locus in low nitrogen tolerant line AH01951 were identified using one, or both, of the following two standard procedures: (1) Plasmid Rescue (Friedrich J. Behringer and June I. Medford. (1992), *Plant Molecular Biology Reporter Vol.* 10, 2:190-198); and (2) Inverse PCR (M. J. McPherson and Philip Quirke. (1991), *PCR: a practical approach*, 137-146). For lines with complex multimerized T-DNA inserts, plasmid rescue and inverse PCR may both prove insufficient to identify candidate genes. In these cases, other procedures, including TAIL PCR (Liu et al. (1995), *Plant J.* 8:457-463) can be employed.

A successful sequencing result is one where a single DNA fragment contains a T-DNA border sequence and flanking genomic sequence. Once a tag of genomic sequence flanking a T-DNA insert is obtained, candidate genes are identified by alignment to publicly available rice genome sequence. Specifically, the annotated gene nearest the 35S enhancer elements/T-DNA RB are candidates for genes that are activated.

To verify that an identified gene is truly near a T-DNA and to rule out the possibility that the DNA fragment is a chimeric cloning artifact, a diagnostic PCR on genomic DNA is done with one oligo in the T-DNA and one oligo specific for the local genomic DNA. Genomic DNA samples that give a PCR product are interpreted as representing a T-DNA insertion. This analysis also verifies a situation in which more than one insertion line occurs in the same line, e.g., if multiple differing genomic fragments are identified in Plasmid Rescue and/or Inverse-PCR analyses.

Genomic DNA was isolated from leaf tissues of the AH01951 line using CTAB method (Murray, M. G. and W. F. Thompson. (1980) *Nucleic Acids Res.*8: 4321-4326).

Ten µg of genomic DNA from AH01951 was digested by 2 µL restriction enzyme Bg/II (NEB). After self-ligation and transformation into competent E. coli DH5a through electroporation, the survived colonies on ampicillin-containing plate were analyzed. After sequencing, the right-border flanking sequence of T-DNA in AH01951 was obtained. This nucleotide sequence was shown as SEQ ID NO: 1.

T-DNA inserted in Chromosome 7 of AH01951's genome, and there are two T-DNA insertion loci in the rice genome of AH01951. One T-DNA inserted in 6960 kb, and there was 26 bp deletion at Right border (RB) of this T-DNA. In the case of AH01951, one gene nearest left border of T-DNA is LOC_Os07g12340.1 (SEQ ID NO: 3), encoding a rice polypeptide annotated as "NAC domain-containing protein 67, putative" in Tigr and referred to herein as OsNAC3/ONAC067 (SEQ ID NO: 5).

The expression levels of OsNAC3/ONAC067 gene in AH01951 line were identified by real-time RT-PCR analyses. Leaf, stem and root samples are collected from AH01951 rice plants at 4-leaf-stage, and the total RNA was extracted using RNAiso Plus kit (TaKaRa) according to manufacturer's instruction separately. The cDNA were prepared by RevertAid™ First Strand cDNA Synthesis Kit (Fermentas) and from 500 ng total RNA. The real-time RT-PCR (SYBR® Premix Ex Taq™, TaKaRa) was conducted using 7,500 Fast real-time RT-PCR equipment and according to the manual (ABI). EF-1α gene was used as an internal control to show that the amplification and loading of samples from the activation tagging line (ATL) and ZH-TC plants are similar. Gene expression was normalized based on the EF1α mRNA levels.

Two primers DP0028-F1 and DP0028-R1 were used for real-time RT-PCR analysis, the primer sequences are as follow:

```
                                            (SEQ ID NO: 10)
DP0028-F1: 5'-GCAGAGCAGGAAGGAGGAG-3'

(SEQ ID NO: 11)
DP0028-R1: 5'-CATCCCCATGAGCCAGTC-3'
```

As shown in FIG. 1, the expression levels of OsNAC3/ONAC067 in roots and stems of AH01591 were up-regulated for about 5 times compared to that of ZH11-TC control respectively, whereas the expression level in the leaves of AH01951 was less than that of ZH11-TC control.

OsNAC3/ONAC067 gene is near the T-DNA insertion locus, and AH01951 line had enhanced low nitrogen tolerance, so this gene was cloned and validated as to its functions in low nitrogen tolerance and other agronomic trait improvement.

Example 6

OsNAC3/ONAC067 Genes Cloning and Over-Expression Vector Construction

Based on the sequences information of gene ID LOC_Os07g12340, two primers were designed for cloning the OsNAC3/ONAC067 gene. The cDNA extracted from leaves of Zhonghua 11 (ZH11) plants was used as template and the cDNA of OsNAC3/ONAC067 was cloned. The PCR reaction mixture and PCR procedure are shown in Table 5 and Table 6. The primers are shown as follow:

```
                                            (SEQ ID NO: 8)
gc-243: 5'-TTCCCTCAAGTCCCAAGATCGAACAC-3'

(SEQ ID NO: 9)
gc-244: 5'-CCATCTGAATTCTGAACTTGCCTGAG-3'
```

TABLE 5

PCR reaction mixture for cloning OsNAC3/ONAC067 gene

| Reaction mix | 50 μL |
| --- | --- |
| Template | 1 μL |
| TOYOBO KOD-FX (1.0 U/μL) | 1 μL |
| 2xPCR buffer for KOD-FX | 25 μL |
| 2 mM dNTPs (0.4 mM each) | 10 μL |
| Primer-F/R (10 μM) | 2 μL each |
| ddH$_2$O | 9 μL |

TABLE 6

PCR cycle conditions for OsNAC3/ONAC067 gene

| 94° C. | 3 min | |
| --- | --- | --- |
| 98° C. | 10 s | |
| 58° C. | 30 s | x30 |
| 68° C. | 1 min | |
| 68° C. | 5 min | |

The PCR amplified DNA fragment of 979 bp in length was extracted after the agarose gel electrophoresis using a column kit and then ligated with TA cloning vectors. The sequence and orientation in the construct was confirmed by sequencing. Then the OsNAC3/ONAC067 gene was transferred to a plant binary construct DP0005 (empty vector, SEQ ID NO: 1) which was digested by restriction enzymes of Bg/II and SalI. The obtained over-expression vectors were named as DP0028 and the OsNAC3/ONAC067 gene was driven by the constitutive promoter CaMV 35S. As described in Example 5 and FIG. 2, the expression level of OsNAC3/NAC067 was higher in root of the AH01951 rice, therefore, a rice root-specific promoter (KT630P) listed as SEQ ID NO: 6 (CN201010547550.7) was used to instead of the constitutive promoter in the construct of DP0028 and the obtained construct was named as DP0224. The cloned nucleotide sequence and coding sequence of OsNAC3/ONAC067 gene are provided as SEQ ID NO: 3 and 4, and the encoded amino acid sequence of OsNAC3/ONAC067 is shown in SEQ ID NO: 5. DsRed gene expression cassette (SEQ ID NO: 7 in the sequence list) was transfer to the plant binary construct DP0005 to get another empty vector DP0158.

Example 7

Transformation Process for Transgenic Rice Lines

All of the over-expression vectors (DP0028 and DP0224) and empty vectors (DP0005 and DP0158) were transformed in the Zhonghua 11 (*Oryza sativa* L.) by *Agrobacteria*-mediated method as described by Lin and Zhang ((2005) *Plant Cell Rep.* 23:540-547). The transgenic seedlings (T$_0$) generated in transformation laboratory were transplanted in the field to get T$_1$ seeds. The T$_1$ and T$_2$ seeds were stored at cold room (4° C.), and T$_2$ seeds were used for following trait screening.

The vector DP0028 in which the OsNAC3/ONAC067 gene was over-expressed under CaMV 35S promoter was used to transform Zhonghua 11 for four times, however, only 84 T$_o$ transgenic seedlings were obtained. Many of these T$_0$ transgenic seedlings were weak, had lower chlorophyll content in leaf and stem, or scattered architecture. Only 7 of the 84 seedlings survived and generated T$_1$ seeds at the harvest season. The transformation efficiency of DP0028 was less than 3% which is more 10-fold lower than that with DP0005 (32%). These indicate that constitutively expressing OsNAC3/ONAC067 gene prevent rice plant regeneration. Therefore, we made DP0224 to over-express OsNAC3/ONAC067 gene under a root-specific promoter KT630P.

DP0224 transgenic rice plants were obtained, most of them did not show abnormal phenotype as DP0028 transgenic plants. So, DP0224 transgenic rice plants were used to perform the following trait screen. T$_1$ DP0224 transgenic rice plants (from 1-2 cm in height) were cultured in 50 mg/L hygromycin solution; and the survived plants (hygromycin-resistant plants) were planted in field to produce T$_2$ seeds. Only the hygromycin-resistant T$_2$ DP0224 transgenic rice was used in trait screen.

The expression levels of the OsNAC3/ONAC067 transgene in roots, stems and leaves of DP0224 transgenic rice plants were analyzed as described in Example 5. As shown in FIG. 2, the expression levels of most of the transgenic lines are higher than the control ZH11-TC in roots, stems and leaves. OsNAC3/ONAC067 gene over-expressed in the DP0224 transgenic rice plants.

Example 8

Low Nitrogen Tolerance Assay of OsNAC3/ONAC067 Transgenic Rice Plants

In order to investigate whether OsNAC3/ONAC067 (DP0224) transgenic rice plants can recapitulate the low nitrogen tolerance phenotype of AH01951 or OsNAC3/ONAC067 gene can improve NUE or the low nitrogen tolerance, the OsNAC3/ONAC067 transgenic rice plants were tested under low nitrogen conditions in greenhouse as described in Example 2.

1) Results of the First Low Nitrogen Tolerance Assay

Eight rice plants of each transgenic line were planted. After growing in modified Hoagland nutrient solution containing 0.75 mM $KNO_3$ for 38-50 days, the tiller number, SPAD value, and fresh weight of OsNAC3/ONAC067 transgenic plants of 11 individual lines and their corresponding segregated negative null seedlings (controls) were measured and analyzed. All of the 11 transgenic lines had greater average fresh weight than their corresponding controls, 4 transgenic lines had significantly greater ($P \leq 0.05$) average fresh weight than the controls (Table 7). And almost all the transgenic lines had greater average tiller numbers or average SPAD values than their segregated nulls. These results demonstrate that the OsNAC3/ONAC067 transgenic plants had enhanced low nitrogen tolerance, and over-expression of OsNAC3/ONAC067 driven by a root-specific promoter can improve the nitrogen use efficiency of rice.

TABLE 7

Low nitrogen tolerance assay of OsNAC3/ONAC067 transgenic rice plants under greenhouse low nitrogen conditions (1$^{st}$ experiment)

| Line ID | Tiller number | | | SPAD value | | | Fresh weight (g) | | |
| --- | --- | --- | --- | --- | --- | --- | --- | --- | --- |
| | Average tiller number | P value | $P \leq 0.05$ | Average SPAD value | P value | $P \leq 0.05$ | Average fresh weight | P value | $P \leq 0.05$ |
| DP0224.02 | 1.3 | 0.5536 | | 33.83 | 0.2733 | | 3.384 | 0.1356 | |
| DP0224.02-Null | 1.1 | | | 32.24 | | | 2.701 | | |
| DP0224.05 | 1.4 | 0.6927 | | 32.25 | 0.5709 | | 3.914 | 0.1057 | |
| DP0224.05-Null | 1.3 | | | 33.29 | | | 2.955 | | |
| DP0224.08 | 2.6 | 0.3159 | | 36.39 | 0.9737 | | 5.241 | 0.0108 | Y |
| DP0224.08-Null | 2.1 | | | 36.36 | | | 3.846 | | |
| DP0224.09 | 2.1 | 0.2894 | | 35.17 | 0.6643 | | 5.161 | 0.0357 | Y |
| DP0224.09-Null | 1.7 | | | 34.74 | | | 3.687 | | |
| DP0224.10 | 2.0 | 0.3506 | | 36.45 | 0.1951 | | 4.963 | 0.0234 | Y |
| DP0224.10-Null | 1.5 | | | 34.83 | | | 3.511 | | |
| DP0224.14 | 2.6 | 0.0082 | Y | 34.90 | 0.4617 | | 4.576 | 0.0200 | Y |
| DP0224.14-Null | 1.1 | | | 36.04 | | | 2.933 | | |
| DP0224.15 | 1.5 | 1.0000 | | 36.03 | 0.8123 | | 4.486 | 0.2940 | |
| DP0224.15-Null | 1.5 | | | 35.70 | | | 3.758 | | |
| DP0224.27 | 1.7 | 0.0989 | | 37.63 | 0.9002 | | 4.689 | 0.5516 | |
| DP0224.27-Null | 1.1 | | | 37.44 | | | 4.334 | | |
| DP0224.31 | 2.0 | 0.6616 | | 36.83 | 0.3953 | | 4.459 | 0.0571 | |
| DP0224.31-Null | 2.3 | | | 36.00 | | | 3.374 | | |

2) Results of the Second Low Nitrogen Tolerance Assay

In the second experiment, ZH11-TC and DP0158 transgenic rice plants were used as controls and 12 transgenic lines were screened. Eight rice plants of each transgenic line were planted. As shown in Table 8, 10 of the 12 transgenic lines had greater average fresh weights than DP0158 controls, and 6 of the 10 transgenic lines had significantly greater average fresh weights ($P \leq 0.05$). In addition, 10 transgenic lines had greater average SPAD values than DP0158 controls, and 7 transgenic lines had greater average tiller number compared to the DP0158 controls. When compared to ZH11-TC controls, most of the 12 transgenic lines had greater average tiller number, average SPAD value and/or average fresh weight. Four transgenic lines (DP0224.08, DP0224.09, DP0224.10 and DP0224.14) had significantly greater ($P \leq 0.05$) fresh weight, and one transgenic line (D0224.27) had significantly greater average SPAD value. These results further demonstrate that OsNAC3/ONAC067 transgenic rice plants had better low nitrogen tolerance compared to either DP0158 rice or ZH11-TC controls.

TABLE 8

Low nitrogen tolerance assay of OsNAC3/ONAC067 transgenic rice plants under greenhouse low nitrogen conditions (2nd experiment)

| Line ID | Tiller number Average tiller number | P value | P ≤ 0.05 | SPAD value Average SPAD value | P value | P ≤ 0.05 | Fresh weight Average fresh weight | P value | P ≤ 0.05 |
|---|---|---|---|---|---|---|---|---|---|
| DP0224.02 | 1.1 | 1.000 | | 39.95 | 0.050 | | 6.485 | 0.059 | |
| DP0158 | 1.1 | | | 37.09 | | | 5.219 | | |
| DP0224.05 | 1.3 | 0.537 | | 40.29 | 0.012 | Y | 7.336 | 0.007 | Y |
| DP0158 | 1.5 | | | 34.11 | | | 4.543 | | |
| DP0224.07 | 1.3 | 0.705 | | 36.65 | 0.363 | | 5.833 | 0.066 | |
| DP0158 | 1.4 | | | 34.21 | | | 4.021 | | |
| DP0224.08 | 1.6 | 0.165 | | 40.83 | 0.088 | | 6.445 | 0.080 | |
| DP0158 | 1.1 | | | 38.33 | | | 5.513 | | |
| DP0224.09 | 1.8 | 0.007 | Y | 38.76 | 0.091 | | 6.788 | 0.000 | Y |
| DP0158 | 1.0 | | | 35.63 | | | 4.209 | | |
| DP0224.10 | 1.4 | 0.295 | | 38.84 | 0.003 | Y | 6.590 | 0.000 | Y |
| DP0158 | 1.1 | | | 34.68 | | | 3.656 | | |
| DP0224.14 | 1.9 | 0.241 | | 40.56 | 0.076 | | 7.308 | 0.000 | Y |
| DP0158 | 1.4 | | | 36.85 | | | 4.888 | | |
| DP0224.15 | 1.0 | 0.714 | | 35.20 | 0.458 | | 6.294 | 0.025 | Y |
| DP0158 | 1.1 | | | 34.14 | | | 4.584 | | |
| DP0224.27 | 1.4 | 0.755 | | 40.44 | 0.023 | Y | 6.846 | 0.002 | Y |
| DP0158 | 1.3 | | | 36.21 | | | 5.144 | | |
| DP0224.31 | 1.5 | 0.035 | Y | 38.94 | 0.056 | | 7.311 | 0.005 | Y |
| DP0158 | 1.0 | | | 35.54 | | | 5.198 | | |

3) Results of the Third Low Nitrogen Tolerance Assay

In the third experiment, ZH11-TC and DP0158 transgenic rice plants were used as controls and ten transgenic lines were tested. Twelve rice plants from each transgenic line, ZH11-TC and DP0158 were planted and repeated twice. The average tiller number, SPAD value and fresh weight of all the OsNAC3/ONAC067 transgenic rice were 1.5, 34.61, and 3.699, respectively. The average fresh weight of OsNAC3/ONAC067 transgenic rice was significantly greater than both ZH11-TC (P value=0.0170) and DP0158 (P value=0.0036) seedlings at construct level.

Analyses at transgenic line level are shown in Table 9 and Table 10. There are no significant differences among the transgenic lines and either the ZH11-TC or DP0158 controls for parameters of average tiller number and SPAD value, whereas, seven transgenic lines exhibited significantly greater fresh weights than the ZH11-TC control, and eight transgenic lines exhibited significantly greater fresh weights than the DP0158 controls. Table 9 and Table 10 clearly demonstrate that OsNAC3/ONAC067 transgenic rice had greater fresh weight at low nitrogen conditions.

TABLE 9

Low nitrogen tolerance assay of OsNAC3/ONAC067 transgenic rice plants under greenhouse low nitrogen conditions (3rd experiment, ZH11-TC was used as control)

| Line ID | Tiller number Average tiller number | P value | P ≤ 0.05 | SPAD value Average SPAD value | P value | P ≤ 0.05 | Fresh weight Average fresh weight | P value | P ≤ 0.05 |
|---|---|---|---|---|---|---|---|---|---|
| DP0224.02 | 1.6 | 0.5289 | | 34.61 | 0.7295 | | 3.252 | 0.6792 | |
| DP0224.05 | 1.6 | 0.4506 | | 34.61 | 0.7296 | | 3.851 | 0.0076 | Y |
| DP0224.08 | 1.7 | 0.1326 | | 34.61 | 0.7296 | | 3.988 | 0.0015 | Y |
| DP0224.09 | 1.7 | 0.2588 | | 34.61 | 0.7296 | | 3.943 | 0.0026 | Y |
| DP0224.10 | 1.5 | 0.8966 | | 34.61 | 0.7295 | | 3.871 | 0.0061 | Y |
| DP0224.14 | 1.5 | 0.8966 | | 34.61 | 0.7295 | | 3.680 | 0.0429 | Y |
| DP0224.15 | 1.4 | 0.9044 | | 34.61 | 0.7295 | | 3.840 | 0.0086 | Y |
| DP0224.27 | 1.3 | 0.4563 | | 34.61 | 0.7295 | | 3.692 | 0.0383 | Y |
| DP0224.31 | 1.5 | 0.9963 | | 34.61 | 0.7295 | | 3.625 | 0.0689 | |
| DP0224.38 | 1.4 | 0.7113 | | 34.61 | 0.7296 | | 3.251 | 0.6801 | |
| ZH11-TC | 1.5 | | | 34.88 | | | 3.142 | | |

TABLE 10

Low nitrogen tolerance assay of OsNAC3/ONAC067 transgenic rice plants under greenhouse low nitrogen conditions (3$^{rd}$ experiment, DP0158 was used as control)

| Line ID | Tiller number | | | SPAD value | | | Fresh weight | | |
|---|---|---|---|---|---|---|---|---|---|
| | Average tiller number | P value | P ≤ 0.05 | Average SPAD value | P value | P ≤ 0.05 | Average fresh weight | P value | P ≤ 0.05 |
| DP0224.02 | 1.6 | 0.8460 | | 34.61 | 0.9729 | | 3.252 | 0.3819 | |
| DP0224.05 | 1.6 | 0.7497 | | 34.61 | 0.9730 | | 3.851 | 0.0017 | Y |
| DP0224.08 | 1.7 | 0.2852 | | 34.61 | 0.9730 | | 3.988 | 0.0003 | Y |
| DP0224.09 | 1.7 | 0.4878 | | 34.61 | 0.9730 | | 3.943 | 0.0005 | Y |
| DP0224.10 | 1.5 | 0.7600 | | 34.61 | 0.9729 | | 3.871 | 0.0013 | Y |
| DP0224.14 | 1.5 | 0.7600 | | 34.61 | 0.9729 | | 3.680 | 0.0129 | Y |
| DP0224.15 | 1.4 | 0.5786 | | 34.61 | 0.9729 | | 3.840 | 0.0020 | Y |
| DP0224.27 | 1.3 | 0.2378 | | 34.61 | 0.9729 | | 3.692 | 0.0113 | Y |
| DP0224.31 | 1.5 | 0.6667 | | 34.61 | 0.9729 | | 3.625 | 0.0226 | Y |
| DP0224.38 | 1.4 | 0.4205 | | 34.61 | 0.9730 | | 3.251 | 0.3825 | |
| DP0158 | 1.5 | | | 34.64 | | | 3.019 | | |

These three experiments consistently demonstrate that OsNAC3/ONAC067 transgenic rice plants exhibited greater fresh weight at low nitrogen conditions, which illustrates that over-expression of OsNAC3/ONAC067 can improve the low nitrogen tolerance or NUE of transgenic plants.

Example 9

Laboratory Chlorate Assay of OsNAC3/ONAC067 Transgenic Rice Plants

Nitrate is a major source of inorganic nitrogen utilized by higher plants. Chlorate is a nitrate analog which can be uptake, transported by same system with nitrogen and reduced to a toxic compound (chlorite) by nitrate reductase (NR) in plants. To further confirm OsNAC3/ONAC067 transgenic rice plants have enhanced NUE, the seedlings were treated with chlorate solution, and seedlings which are sensitive to chlorate are considered to have better NUE or low nitrogen tolerance.

Chlorate Assay Method

In this assay, ten OsNAC3/ONAC067 transgenic lines were tested, and ZH11-TC and DP0158 transgenic plants were used as controls.

T$_2$ transgenic seeds were sterilized and germinated as description in Example 2, and this assay was performed in culture room with temperature at 28-30° C. and humidity around 30%. The germinated seeds were placed in a tube with a hole at the bottom, and water cultured at 30° C. for 6 days till one-leaf and one-terminal bud stage. Uniform seedlings about 5.5 cm in height were selected for the chlorate screening. Randomized block design was used in this experiment. There were five blocks in one container. Each transgenic line was placed in one row (12 plants/line), and ZH11-TC and DP0158 seedlings were placed in 3 rows (3×12 plants) randomly in one block. Then the seedlings were cultured in 0.4 mM chlorate solution for 5 days at 10 h light/14 h dark, the treated seedlings first encountered night and uptake the chlorate solution which was changed on the third day. After 5-day treatment, the seedlings were then cultured in 1/10Hoagland's solution (Table 2) for 4 days. The seedlings with withered leaves and totally without green are counted as sensitive; while the seedlings only with necrosed leaves or stem, or bleached leaves are not considered to be sensitive seedlings.

Sensitive rate was used as a parameter for this screen, which is the percentage of the number of sensitive plants over the total plant number.

The data was analyzed at construct level (all transgenic plants compared to the control) and transgenic line level (different transgenic lines compared to the control, separately) using a statistic model of "Y~seg+line(seg)+rep+error", with random effect: "rep"; Statistic Method: "SAS Proc Glimmix".

Chlorate Assay Results

Chlorate assay were performed twice to test the chlorate sensitivity of OsNAC3/ONAC067 transgenic rice.

1) Results of the First Chlorate Assay

After treated with 0.4 mM chlorate solution for 5 days and cultured in 1/10Hoagland solution for 4 days, 409 of 600 OsNAC3/ONAC067 transgenic seedlings (74%) died, while only 101 of 192 (53%) DP0158 seedlings died, and 130 of 216 (60%) of ZH11-TC seedlings died. The sensitive rate of OsNAC3/ONAC067 transgenic seedlings was significantly (P value=0.0000) higher than that of the DP0158 control and ZH11-TC control. These results indicate that the OsNAC3/ONAC067 transgenic seedlings have enhanced chlorate sensitive compared to both DP0158 and ZH11-TC controls at construct level.

Further analysis at the transgenic line level displayed in Table 11, 10 transgenic lines were screened by chlorate solution, the sensitive rates of 9 transgenic lines were higher than that of the DP0158 seedlings, and the sensitive rates of 8 transgenic lines were significantly higher than that of DP0158 seedlings. The sensitive rates of 8 transgenic lines were also higher than that of the ZH11-TC. These results demonstrate that DP0224 transgenic rice plants have enhanced chlorate sensitive at construct and transgenic line level at seedling stages.

TABLE 11

Chlorate sensitive assay of OsNAC3/ONAC067 transgenic rice seedlings at the transgenic line level (1st experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0224.05 | 57 | 60 | 95 | 0.0000 | Y | 0.0000 | Y |
| DP0224.08 | 44 | 60 | 73 | 0.0615 |   | 0.0069 | Y |
| DP0224.09 | 53 | 60 | 88 | 0.0003 | Y | 0.0000 | Y |
| DP0224.10 | 36 | 60 | 60 | 0.9804 |   | 0.3199 |   |
| DP0224.14 | 27 | 36 | 75 | 0.0728 |   | 0.0138 | Y |
| DP0224.15 | 50 | 60 | 83 | 0.0018 | Y | 0.0002 | Y |
| DP0224.27 | 20 | 36 | 56 | 0.6848 |   | 0.6967 |   |
| DP0224.31 | 45 | 60 | 75 | 0.0365 | Y | 0.0037 | Y |
| DP0224.37 | 31 | 60 | 52 | 0.2604 |   | 0.8951 |   |
| DP0224.38 | 46 | 60 | 77 | 0.0206 | Y | 0.0020 | Y |
| ZH11-TC | 130 | 216 | 60 |   |   |   |   |
| DP0158 | 101 | 192 | 53 |   |   |   |   |

2) Results of the Second Chlorate Assay

After treated with 0.4 mM chlorate solution for 5 days and cultured in 1/10Hoagland solution for 4 days, 259 of 468 OsNAC3/ONAC067 transgenic seedlings (55%) died, while 127 of 312 (41%) ZH11-TC seedlings died, and 61 of 180 (34%) DP0158 seedlings died. The sensitive rate of OsNAC3/ONAC067 transgenic seedlings was significantly higher than that of the ZH11-TC (P value=0.0001) control and DP0158 (P value=0.0000) control. These results further indicate that the OsNAC3/ONAC067 transgenic seedlings have enhanced chlorate sensitive rate compared to both DP0158 and ZH11-TC controls at the construct level.

Analysis at the transgenic line level showed that the Chlorate sensitive rates of six transgenic lines were higher than both of ZH11-TC and DP0158 seedlings, and the sensitive rates of five transgenic lines were significantly higher than both of ZH11-TC and DP0158 seedlings. These results consistently demonstrate that OsNAC3/ONAC067 transgenic rice plants have enhanced chlorate sensitive at construct and transgenic line level at seedling stages.

There are many OsNAC3/ONAC067 transgenic lines exhibited enhanced low nitrogen tolerance under greenhouse conditions (Example 8) and enhanced chlorate sensitivity (Table 9). These cross-validations of the same lines by two different assays clearly and consistently demonstrate the increased low nitrogen tolerance or NUE of OsNAC3/ONAC067 transgenic rice plants.

Example 10

Field Low Nitrogen Assay of OsNAC3/ONAC067 Transgenic Rice Plants

Field low nitrogen assay was performed in Beijing. OsNAC3/ONAC067 transgenic rice plants were planted in low nitrogen field, and fertilizer without nitrogen was used in the whole growth period. Seed germination and seedling culturing were performed as described in Example 2. At 3-leaf stage, the seedlings were transplanted into the testing fields, with 4 replicates and 10 plants per replicate for each

TABLE 12

Chlorate sensitive assay of OsNAC3/ONAC067 transgenic rice seedlings at the transgenic line level (2nd experiment)

| Line ID | Number of dead seedlings | Number of total seedlings | Sensitive rate (%) | CK = ZH11-TC P value | P ≤ 0.05 | CK = DP0158 P value | P ≤ 0.05 |
|---|---|---|---|---|---|---|---|
| DP0224.05 | 38 | 60 | 63 | 0.0024 | Y | 0.0002 | Y |
| DP0224.08 | 22 | 60 | 37 | 0.5612 |   | 0.6964 |   |
| DP0224.09 | 40 | 60 | 67 | 0.0006 | Y | 0.0000 | Y |
| DP0224.10 | 24 | 60 | 40 | 0.9193 |   | 0.3950 |   |
| DP0224.15 | 35 | 60 | 58 | 0.0153 | Y | 0.0016 | Y |
| DP0224.27 | 34 | 48 | 71 | 0.0004 | Y | 0.0000 | Y |
| DP0224.31 | 34 | 60 | 57 | 0.0270 | Y | 0.0030 | Y |
| DP0224.38 | 32 | 60 | 53 | 0.0765 |   | 0.0101 | Y |
| ZH11-TC | 127 | 312 | 41 |   |   |   |   |
| DP0158 | 61 | 180 | 34 |   |   |   |   |

The above two experiments consistently demonstrate that over-expression of OsNAC3/ONAC067 under a root-specific promoter increased the chlorate sensitivity of transgenic plants by increasing chlorate uptake, transport and/or reduction by nitrate reductase in leaf and stem tissues. These results indirectly further show that over-expression of OsNAC3/ONAC067 improved low nitrogen tolerance or NUE of the transgenic rice.

transgenic line, and the 4 replicates are planted in the same block. The ZH11-TC and DP0158 plants nearby are used as controls in the statistical analysis.

The rice plants were managed by normal practice using pesticides, but applying phosphor fertilizer and potassium fertilizer for N-0 treatment testing field during the whole growth period. The stem thickness of the main stem at 10 cm above the earth was measured by electronic digital calipers during heading stage; the plant height which is the length from the stem base to the panicle base was measure before harvest.

At the end of the season, about six representative plants of each transgenic line were harvested from the middle of the row per line. The panicles first were cut and store in one bag, and then the stems were cut above the earth and put in another bag. The total panicle number per plant was obtained by counting, and the panicle weight per plant and yield per plant was measured. After air-drying, the biomass was obtained by weighting the stems. The stem thickness, plant height, biomass and grain yield data were statistically analyzed using mixed linear model by ASRemI program.

Results of Field Low Nitrogen Assay

TABLE 13

Grain yield analysis of OsNAC3/ONAC067 transgenic rice under low nitrogen conditions during the whole growth period

| Line ID | Number of survival plant | Number of harvested plant | Grain yield per plant (g) | CK = ZH11-TC P value | P ≤ 0.1 | CK = DP0158 P value | P ≤ 0.1 |
|---|---|---|---|---|---|---|---|
| DP0224.02 | 38 | 24 | 36.92 | 0.046 | Y | 0.002 | Y |
| DP0224.04 | 40 | 23 | 33.29 | 0.750 |   | 0.137 |   |
| DP0224.05 | 40 | 24 | 33.66 | 0.623 |   | 0.098 | Y |
| DP0224.07 | 39 | 18 | 31.35 | 0.564 |   | 0.554 |   |
| DP0224.08 | 39 | 23 | 32.82 | 0.919 |   | 0.205 |   |
| DP0224.10 | 40 | 22 | 33.48 | 0.682 |   | 0.114 |   |
| DP0224.21 | 40 | 24 | 36.15 | 0.101 |   | 0.005 | Y |
| DP0224.31 | 39 | 24 | 32.49 | 0.960 |   | 0.263 |   |
| DP0224.36 | 40 | 23 | 34.00 | 0.516 |   | 0.070 | Y |
| DP0224.40 | 39 | 23 | 32.69 | 0.966 |   | 0.229 |   |
| DP0224.41 | 40 | 22 | 34.08 | 0.492 |   | 0.064 | Y |
| ZH11-TC | 40 | 23 | 32.60 |   |   |   |   |
| DP0158 | 40 | 24 | 30.07 |   |   |   |   |

TABLE 14

Biomass analysis of OsNAC3/ONAC067 transgenic rice under low nitrogen conditions during the whole growth period

| Line ID | Number of survival plant | Number of harvested plant | Biomass (g) | CK = ZH11-TC P value | P ≤ 0.1 | CK = DP0158 P value | P ≤ 0.1 |
|---|---|---|---|---|---|---|---|
| DP0224.02 | 38 | 24 | 26.76 | 0.030 | Y | 0.051 | Y |
| DP0224.04 | 40 | 23 | 24.25 | 0.500 |   | 0.647 |   |
| DP0224.05 | 40 | 24 | 26.81 | 0.029 | Y | 0.049 | Y |
| DP0224.07 | 39 | 18 | 24.88 | 0.292 |   | 0.404 |   |
| DP0224.08 | 39 | 23 | 25.88 | 0.101 |   | 0.155 |   |
| DP0224.10 | 40 | 22 | 26.23 | 0.065 | Y | 0.103 |   |
| DP0224.21 | 40 | 24 | 27.31 | 0.013 | Y | 0.023 | Y |
| DP0224.31 | 39 | 24 | 25.34 | 0.186 |   | 0.270 |   |
| DP0224.36 | 40 | 23 | 27.02 | 0.021 | Y | 0.036 | Y |
| DP0224.40 | 39 | 23 | 25.43 | 0.171 |   | 0.249 |   |
| DP0224.41 | 40 | 22 | 26.39 | 0.051 | Y | 0.084 | Y |
| ZH11-TC | 40 | 23 | 23.11 |   |   |   |   |
| DP0158 | 40 | 24 | 23.48 |   |   |   |   |

TABLE 15

Stem thickness analysis of OsNAC3/ONAC067 transgenic rice under low nitrogen conditions

| Line ID | Number of survival plant | Number of tested plant | Stem thickness (mm) | CK = ZH11-TC P value | P ≤ 0.1 | CK = DP0158 P value | P ≤ 0.1 |
|---|---|---|---|---|---|---|---|
| DP0224.02 | 38 | 24 | 8.67 | 0.000 | Y | 0.000 | Y |
| DP0224.04 | 40 | 23 | 8.77 | 0.000 | Y | 0.000 | Y |
| DP0224.05 | 40 | 24 | 8.70 | 0.000 | Y | 0.000 | Y |
| DP0224.07 | 39 | 18 | 8.59 | 0.000 | Y | 0.000 | Y |
| DP0224.08 | 39 | 23 | 8.71 | 0.000 | Y | 0.000 | Y |
| DP0224.10 | 40 | 22 | 8.73 | 0.000 | Y | 0.000 | Y |
| DP0224.21 | 40 | 24 | 8.63 | 0.000 | Y | 0.000 | Y |
| DP0224.31 | 39 | 24 | 8.91 | 0.000 | Y | 0.000 | Y |
| DP0224.36 | 40 | 23 | 8.79 | 0.000 | Y | 0.000 | Y |
| DP0224.40 | 39 | 23 | 8.75 | 0.000 | Y | 0.000 | Y |

TABLE 15-continued

Stem thickness analysis of OsNAC3/ONAC067 transgenic rice under low nitrogen conditions

| Line ID | Number of survival plant | Number of tested plant | Stem thickness (mm) | CK = ZH11-TC | | CK = DP0158 | |
|---|---|---|---|---|---|---|---|
| | | | | P value | P ≤ 0.1 | P value | P ≤ 0.1 |
| DP0224.41 | 40 | 22 | 8.80 | 0.000 | Y | 0.000 | Y |
| ZH11-TC | 40 | 23 | 7.48 | | | | |
| DP0158 | 40 | 24 | 7.58 | | | | |

TABLE 16

Plant height analysis of OsNAC3/ONAC067 transgenic rice under low nitrogen conditions during the whole growth period

| Line ID | Number of survival plant | Number of harvested plant | Height (cm) | CK = ZH11-TC | | CK = DP0158 | |
|---|---|---|---|---|---|---|---|
| | | | | P value | P ≤ 0.1 | P value | P ≤ 0.1 |
| DP0224.02 | 38 | 24 | 122.72 | 0.000 | Y | 0.000 | Y |
| DP0224.04 | 40 | 23 | 114.51 | 0.286 | | 0.003 | Y |
| DP0224.05 | 40 | 24 | 121.82 | 0.000 | Y | 0.000 | Y |
| DP0224.07 | 39 | 18 | 111.34 | 0.225 | | 0.520 | |
| DP0224.08 | 39 | 23 | 121.94 | 0.000 | Y | 0.000 | Y |
| DP0224.10 | 40 | 22 | 126.37 | 0.000 | Y | 0.000 | Y |
| DP0224.21 | 40 | 24 | 121.68 | 0.000 | Y | 0.000 | Y |
| DP0224.31 | 39 | 24 | 127.99 | 0.000 | Y | 0.000 | Y |
| DP0224.36 | 40 | 23 | 121.58 | 0.000 | Y | 0.000 | Y |
| DP0224.40 | 39 | 23 | 125.03 | 0.000 | Y | 0.000 | Y |
| DP0224.41 | 40 | 22 | 125.95 | 0.000 | Y | 0.000 | Y |
| ZH11-TC | 40 | 23 | 113.05 | | | | |
| DP0158 | 40 | 24 | 110.44 | | | | |

Analysis at construct level demonstrate that the average grain yield per plant, biomass per plant, stem thickness of main stem and plant height of all the OsNAC3/ONAC067 transgenic rice plant were 33.72 g, 26.03 g, 8.73 mm, and 121.90 cm, respectively. The average grain yield per plant was significantly greater than DP0158 control, and the average biomass per plant, stem thickness of main stem and plant height were significantly higher than both of ZH11-TC and DP0158 controls.

As shown in Table 13-16, five transgenic lines exhibited greater grain yield per plant than DP0158 control. Most transgenic lines showed significant greater biomass per plant than both controls, and almost all transgenic lines had greater stem thickness and plant height. These results demonstrate that OsNAC3/ONAC067 transgenic rice exhibited enhanced low nitrogen tolerance in the field. OsNAC3/ONAC067 gene can be used to improve low nitrogen tolerance or NUE, and to improve grain yield of transgenic plants.

Example 11

Drought Tolerance Assay of OsNAC3/ONAC067 Transcenic Rice Plants Under Greenhouse Conditions Drought tolerance assay was performed in greenhouse to investigate whether the OsNAC3/ONAC067 transgenic rice plants had drought tolerance. The GH environment was same as that described in Example 2.
Drought Screening Method:
T₂ Transgenic seeds were sterilized and germinated as described in Example 2. The germinated seeds were sowed in one tray filled with mixture of organic soil, vermiculite and sand (V:V:V=3:3:2). Randomized block design was used. The seedlings were grown under normal greenhouse condition and watered by modified IRRI solution. When the seedlings grew to 3-leaf stage, watering was stopped and the trays were kept in a dry place until the leaves became dry and curved (approximately 9-15 days depending on the seasons). The trays were transferred into water pool to recover the seedlings for 5-7 days, and then plants were scored for the degree of recovery. The following scoring system was used: more than half green stem=1, more than two thirds green leaf=1, less than two thirds but more than one third green leaf=0.5, less than one third green leaf=0.2, no green leaf or less than half green stem=0. The recovery degree was the sum of the score of the green tissues. Survival rate which is percentage of survived plants over the total plant number was also used as a parameter for drought tolerance assay. In this experiment, nine transgenic lines were planted in one experimental unit to evaluate the transgene at construct level by Mixed Model considering construct, line and environment effects. If the survival rates or recovery degrees of the transgenic rice plants were significantly greater than control (P<0.05), the gene was considered to have drought tolerance.
GH Drought Assay Results:
Nine OsNAC3/ONAC067 transgenic lines and both of ZH11-TC and DP0158 controls were planted in one tray and repeated for three times. When the seedlings grew to 3-leaf stage, these three trays were removed to dry place. After drying for 16 or 17 days, these trays were removed to water pool, and after recovered for 5 or 6 days, the average recovery degrees and survival rates were calculated. As shown in Table 17, 183 of 324 transgenic rice plants survived; while, 25 of 72 ZH11-TC seedlings and 10 of 36 DP0158 seedlings survived. The survival rate and the average recovery degree of OsNAC3/ONAC067 transgenic rice were greater than both ZH11-TC and DP0158 controls. These results indicate that OsNAC3/ONAC067 transgenic rice exhibited improved drought tolerance at seedling stage.

TABLE 17

Drought tolerance assay of OsNAC3/ONAC067 transgenic rice plants under greenhouse drought conditions (at construct level)

| Line ID | Number of survival seedling | Number of total seedling | Survival rate (%) | Average recovery degree | P value | P ≤ 0.05 |
|---------|---|---|---|---|---|---|
| DP0224  | 183 | 324 | 56.5 | 0.75 | 0.0439 | Y |
| ZH11-TC | 25  | 72  | 34.7 | 0.50 | | |
| DP0224  | 183 | 324 | 56.5 | 0.75 | 0.0662 | |
| DP0158  | 10  | 36  | 27.8 | 0.47 | | |

Further analysis at the transgenic line level showed that eight lines exhibited greater survival rates and average recovery degrees, five lines exhibited significantly greater average recovery degrees compared to ZH11-TC control and four lines exhibited significantly greater recovery degrees compared to DP0158 control (Table 18). These results clearly demonstrate that over-expression OsNAC3/ONAC067 enhanced the drought tolerance of transgenic rice plants at seedlings stage.

TABLE 18

Drought tolerance assay of OsNAC3/ONAC067 transgenic rice plants under greenhouse drought conditions (at transgenic line level)

| Line ID | Number of survival seedling | Number of total seedling | Survival rate (%) | Average recovery degree | CK = ZH11-TC | | CK = DP0158 | |
|---------|---|---|---|---|---|---|---|---|
| | | | | | P value | P ≤ 0.05 | P value | P ≤ 0.05 |
| DP0224.02 | 17 | 36 | 47.2 | 0.73 | 0.1051 | | 0.1193 | |
| DP0224.05 | 17 | 36 | 47.2 | 0.61 | 0.4566 | | 0.4154 | |
| DP0224.07 | 11 | 36 | 30.6 | 0.44 | 0.6568 | | 0.8458 | |
| DP0224.08 | 28 | 36 | 77.8 | 1.02 | 0.0002 | Y | 0.0010 | Y |
| DP0224.10 | 26 | 36 | 72.2 | 0.90 | 0.0045 | Y | 0.0095 | Y |
| DP0224.28 | 14 | 36 | 38.9 | 0.52 | 0.8810 | | 0.7568 | |
| DP0224.31 | 21 | 36 | 58.3 | 0.78 | 0.0498 | Y | 0.0646 | |
| DP0224.36 | 21 | 36 | 58.3 | 0.81 | 0.0300 | Y | 0.0429 | Y |
| DP0224.40 | 28 | 36 | 77.8 | 0.92 | 0.0028 | Y | 0.0066 | Y |
| ZH11-TC | 25 | 72 | 34.7 | 0.50 | | | | |
| DP0158 | 10 | 36 | 27.8 | 0.47 | | | | |

Example 12

Laboratory Paraquat Assay of OsNAC3/ONAC067 Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress and cold stress usually leads to increased reactive oxygen species (ROS) in plants and sometimes, the drought and/or cold tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant transgenic rice plants was tested.

Paraquat Assay Methods:

Transgenic rice plants from ten transgenic lines were tested by paraquat assay. Tissue-cultured Zhonghua 11 plants (ZH11-TC) and empty vector transgenic plants (DP0158) were used as controls. $T_2$ transgenic seeds were sterilized and germinated as described in Example 2, and this assay was carried out in growth room with temperature at 28-30° C. and humidity ~30%. The germinated seeds were placed in a tube with a hole at the bottom, and water cultured at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 µM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS Proc Glimmix".

Paraquat Assay Results:

OsNAC3/ONAC067 transgenic rice plants were tested for three times.

1) Results of the First Paraquat Assay

After treated with paraquat solution for 7 days, 320 of 576 OsNAC3/ONAC067 transgenic seedlings (56%) kept green and showed tolerant phenotype, while 61 of 204 (30%) ZH11-TC seedlings showed tolerant phenotype, and 98 of 180 (54%) of DP0158 seedlings showed tolerant phenotype. The tolerance rate of OsNAC3/ONAC067 transgenic seedlings was significantly (P value=0.0000) higher than that of the ZH11-TC control. These results indicate that the OsNAC3/ONAC06 transgenic seedlings have enhanced paraquat tolerance rate compared to ZH11-TC control at construct level.

Further analysis at transgenic line level displayed in Table 19, eight lines had significantly higher tolerance rates than ZH11-TC seedlings, and two lines had significantly higher tolerance rates than DP0158 seedlings. These results demonstrate that OsNAC3/ONAC067 transgenic rice plants have enhanced paraquat tolerance at construct and transgenic line level at seedling stages.

TABLE 19

Paraquat tolerance assay of OsNAC3/ONAC067 transgenic rice seedlings at transgenic lines level ($1^{st}$ experiment)

| Line ID | Number of tolerant plant | Number of total plant | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0224.02 | 23 | 60 | 38 | 0.2300 | | 0.0353 | |
| DP0224.05 | 41 | 60 | 68 | 0.0000 | Y | 0.0648 | |
| DP0224.08 | 30 | 60 | 50 | 0.0063 | Y | 0.5516 | |
| DP0224.09 | 49 | 60 | 82 | 0.0000 | Y | 0.0006 | Y |
| DP0224.10 | 32 | 60 | 53 | 0.0017 | Y | 0.8821 | |
| DP0224.14 | 16 | 60 | 27 | 0.6186 | | 0.0006 | |
| DP0224.15 | 29 | 60 | 48 | 0.0115 | Y | 0.4138 | |
| DP0224.27 | 28 | 36 | 78 | 0.0000 | Y | 0.0182 | Y |
| DP0224.31 | 36 | 60 | 60 | 0.0001 | Y | 0.4540 | |
| DP0224.38 | 36 | 60 | 60 | 0.0001 | Y | 0.4585 | |
| ZH11-TC | 61 | 204 | 30 | | | | |
| DP0158 | 98 | 180 | 54 | | | | |

2) Results of the Second Paraquat Assay

In the second experiment, after treated with paraquat solution, 410 of all 600 transgenic seedlings kept green and tolerant phenotype, the tolerance rate was 68%; whereas, 116 of 180 ZH11-TC seedlings kept green and 111 of 180 DP0158 seedlings kept green. The paraquat tolerance rates of ZH11-TC and DP0158 were 64% and 62%. The paraquat tolerance rate of OsNAC3/ONAC067 transgenic rice was significantly higher than DP0158 seedlings (P value=0.0511). The results demonstrate that the OsNAC3/ONAC067 transgenic seedlings have enhanced paraquat tolerance rate compared to DP0158 control at construct level.

Analysis at transgenic line level showed that the paraquat tolerance rates of six lines were higher than that of both ZH11-TC and DP0158 controls, wherein the P value of four lines reached the significant level (Table 20).

TABLE 20

Paraquat tolerance assay of OsNAC3/ONAC067 transgenic rice seedlings at transgenic lines level ($2^{nd}$ experiment)

| Line ID | Number of tolerant plant | Number of total plant | Tolerance rate (%) | CK = ZH11-TC | | CK = DP0158 | |
|---|---|---|---|---|---|---|---|
| | | | | P value | P ≤ 0.05 | P value | P ≤ 0.05 |
| DP0224.02 | 42 | 60 | 70 | 0.4341 | | 0.2490 | |
| DP0224.05 | 37 | 60 | 62 | 0.6985 | | 1.0000 | |
| DP0224.07 | 31 | 60 | 52 | 0.0839 | | 0.1772 | |
| DP0224.08 | 35 | 60 | 58 | 0.3982 | | 0.6476 | |
| DP0224.10 | 47 | 60 | 78 | 0.0520 | Y | 0.0230 | Y |
| DP0224.27 | 31 | 60 | 52 | 0.0839 | | 0.1772 | |
| DP0224.28 | 48 | 60 | 80 | 0.0302 | Y | 0.0129 | Y |
| DP0224.31 | 40 | 60 | 67 | 0.7552 | | 0.4890 | |
| DP0224.36 | 52 | 60 | 87 | 0.0027 | Y | 0.0011 | Y |
| DP0224.38 | 47 | 60 | 78 | 0.0527 | Y | 0.0233 | Y |
| ZH11-TC | 116 | 180 | 64 | | | | |
| DP0158 | 111 | 180 | 62 | | | | |

3) Results of the Third Paraquat Assay

In the third experiment, 288 of 552 transgenic seedlings kept green and showed tolerant phenotype after paraquat solution treated, the paraquat tolerance rate was 52%. 98 of 228 ZH11-TC seedlings and 75 of 180 DP0158 seedlings kept green and showed tolerant phenotype, and the paraquat tolerance rates of ZH11-TC and DP0158 were 43% and 42%. The paraquat tolerance rate of OsNAC3/ONAC067 transgenic rice was significantly higher than both ZH11-TC (P value=0.0056) and DP0158 (P value=0.0045) seedlings. The third experiment further demonstrates that OsNAC3/ONAC067 transgenic rice exhibited better paraquat tolerance.

Analysis at the transgenic line level was displayed in Table 21. Seven lines had higher paraquat tolerance rates than both ZH11-TC and DP0158 controls, and the differences between five transgenic lines and controls of ZH11-TC and DP0158 had reached significant level. These results clearly demonstrate that OsNAC3/ONAC067 transgenic rice exhibited better paraquat tolerance.

TABLE 21

Paraquat tolerance assay of OsNAC3/ONAC067 transgenic rice seedlings at transgenic lines level ($3^{rd}$ experiment)

| Line ID | Number of tolerant plant | Number of total plant | Tolerance rate (%) | CK = ZH11-TC P value | P ≤ 0.05 | CK = DP0158 P value | P ≤ 0.05 |
|---|---|---|---|---|---|---|---|
| DP0224.02 | 37 | 60 | 62 | 0.0132 | Y | 0.0099 | Y |
| DP0224.05 | 20 | 60 | 33 | 0.1827 |   | 0.2585 |   |
| DP0224.07 | 38 | 60 | 63 | 0.0074 | Y | 0.0055 | Y |
| DP0224.08 | 37 | 60 | 62 | 0.0132 | Y | 0.0099 | Y |
| DP0224.10 | 30 | 60 | 50 | 0.3349 |   | 0.2650 |   |
| DP0224.27 | 10 | 12 | 83 | 0.0190 | Y | 0.0164 | Y |
| DP0224.28 | 25 | 60 | 42 | 0.8551 |   | 1.0000 |   |
| DP0224.31 | 24 | 60 | 40 | 0.6789 |   | 0.8211 |   |
| DP0224.36 | 28 | 60 | 47 | 0.6107 |   | 0.5008 |   |
| DP0224.38 | 39 | 60 | 65 | 0.0040 | Y | 0.0030 | Y |
| ZH11-TC | 98 | 228 | 43 |   |   |   |   |
| DP0158 | 75 | 180 | 42 |   |   |   |   |

Overall, OsNAC3/ONAC067 transgenic rice exhibited better paraquat tolerance at both construct and line levels. Over-expression of OsNAC3/ONAC067 under a root-specific promoter increased the paraquat tolerance of transgenic plants. These results indirectly further show that over-expression of OsNAC3/ONAC067 improved drought tolerance of the transgenic rice.

Example 13

Transformation and Evaluation of Maize with Rice OsNAC3/ONAC067 Genes

Maize plants can be transformed to over-express *Oryza sativa* OsNAC3/ONAC067 genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., Mol. Breed. 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as $T_1$ plants, can be subjected to a soil-based low nitrogen stress. Using image analysis, plant area, volume, growth rate and color can be measured at multiple times before and during nitrogen limiting conditions. Significant delay in leaf area reduction, a reduced yellow-color accumulation, and/or an increased growth rate during nitrogen limiting conditions, relative to a control, will be considered evidence that the OsNAC3/ONAC067 functions in maize to enhance NUE.

Example 14

Transformation and Evaluation of Gaspe Flint Derived Maize Lines

As described in example 9, maize plants can be transformed to over-express the rice OsNAC3/ONAC067 gene, or a corresponding homolog from another species. In certain circumstances, recipient plant cells can be from a uniform maize line which having a short life cycle ("fast cycling"), a reduced size, and high transformation potential, and are disclosed in Tomes et al. U.S. Pat. No. 7,928,287.

The population of transgenic ($T_0$) plants resulting from the transformed maize embryos can be grown in a controlled greenhouse environment using a modified randomized block design to reduce or eliminate environmental error. For example, a group of 30 plants, comprising 24 transformed experimental plants and 6 control plants (collectively, a "replicate group"), are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of 30 plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

Each plant in the line population is identified and tracked throughout the evaluation process, and the data gathered from that plant are automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor (U.S. Pat. Nos. 7,403,855 and 7,702,462).

Each greenhouse plant in the $T_0$ line population, including any control plants, is analyzed for agronomic characteristics of interest, and the agronomic data for each plant are recorded or stored in a manner so as to be associated with the identifying data for that plant. Confirmation of a phenotype (gene effect) can be accomplished in the $T_1$ generation with a similar experimental design to that described above.

Example 15

Laboratory NUE Screening of Rice OsNAC3/ONAC067 Gene in *Arabidopsis*

To understand whether rice OsNAC3/ONAC067 gene can improve dicot plants' nitrogen stress tolerance, or other traits, rice OsNAC3/ONAC067 gene over-expression vectors were transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1:641-646).

The vector DP0028 was used to transform *Arabidopsis* Columbia, the transformation efficiency was low, only two transgenic lines were got, and the $T_0$ transgenic *Arabidopsis* showed special phenotype such as widener and bigger rosette leaf at vegetative stage, more bolts, and Leaf senescence at reproductive stage. It was not used to perform the nitrogen stress tolerance.

The OsNAC3/ONAC067 gene driven by a root-specific or root-preferred promoter is further used to validate the low nitrogen tolerance of the OsNAC3/ONAC067 gene in *Arabidopsis*.

The $T_1$ fluorescent seeds were selected, surface sterilized and stratified in the dark at 4° C. for three days. Then 32 $T_2$ individuals were sown next to 32 empty vector control (pBCyellow-empty vector) individuals on one low nitrogen media containing 0.5×N-Free Hoagland's, 0.4 mM potassium nitrate, 0.1% sucrose, 1 mM MES and 0.25% Phytagel™ as shown in Table 6. Two repeats are prepared. The plates were horizontally placed in the growth chamber and cultured for a period of 10 days at 22° C., 60% relative humidity and a 16 hour day cycle. Seedling status was evaluated by imaging the entire plate from 10-13 days after stratifications.

The images were analyzed using Nitrosight software and the number of Pixel (for size of the plants) and the intensity of Bin2 (for green color of leaves) for each of the 32/64 transgenic seedlings were compared with 32/64 seedlings of empty vector control for similar parameters. The green color and better growth of the seedling as compared to the empty vector control seedling signifies improved NUE. The data was statistically analyzed and a P value of lower than $10^{-3}$ was considered as a validation of the gene for NUE. In this experiment, the information from Genomix LeadTracker is views as statistically significant for the mutant by $10^{-5}$ or more, and statistically significant for the mutant by $10^{-3}$.

What is claimed is:

1. A method of increasing nitrogen stress tolerance in a plant, comprising:
   (a) expressing in a regenerable plant cell a polynucleotide operably linked to at least one heterologous regulatory sequence, wherein the polynucleotide encodes a polypeptide having an amino acid sequence of at least 99% sequence identity to SEQ ID NO: 5 and the expression level of the polynucleotide is increased compared to that of a control plant; and
   (b) generating a plant from the regenerable plant cell of part (a); and
   (c) selecting a plant generated in part (b) comprising the polynucleotide operably linked to the heterologous regulatory element for increased nitrogen stress tolerance as compared to a control plant not comprising the polynucleotide operably linked to the heterologous regulatory element.

2. The method of claim 1, wherein the selected plant shows an increase in grain yield.

3. The method of claim 1, wherein the polynucleotide comprises the nucleotide sequence of SEQ ID NO: 3 or SEQ ID NO: 4.

4. The method of claim 1, wherein the polynucleotide encodes a polypeptide comprising SEQ ID NO: 5.

5. The method of claim 1, wherein the regulatory sequence is a promoter functional in a plant.

6. The method of claim 5, wherein the promoter is a tissue-preferred promoter.

7. The method of claim 6, wherein the tissue-specific promoter is a root-preferred promoter of SEQ ID NO: 6.

8. The method of claim 1, wherein said plant is selected from the group consisting of rice, maize, soybean, sunflower, sorghum, canola, wheat, alfalfa, cotton, barley, millet, sugar cane and switchgrass.

* * * * *